(12) United States Patent
Wyatt et al.

(10) Patent No.: US 6,753,462 B2
(45) Date of Patent: Jun. 22, 2004

(54) TRANSGENIC PLANTS WITH INCREASED CALCIUM STORES

(75) Inventors: Sarah Wyatt, Raleigh, NC (US); Pei-Lan Tsou, Raleigh, NC (US); Dominique Robertson, Cary, NC (US); Wendy Boss, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 168 days.

(21) Appl. No.: 09/844,006

(22) Filed: Apr. 27, 2001

(65) Prior Publication Data

US 2002/0083496 A1 Jun. 27, 2002

Related U.S. Application Data

(60) Provisional application No. 60/200,233, filed on Apr. 28, 2000.

(51) Int. Cl.[7] ........................... C12N 15/82; A01H 5/00; A01H 5/08; A01H 5/10
(52) U.S. Cl. ....................... 800/289; 800/298; 800/288; 800/300; 435/419; 435/69.8
(58) Field of Search ................................. 800/298, 289, 800/300, 288; 435/418, 69.8

(56) References Cited

FOREIGN PATENT DOCUMENTS

WO   WO 98/36084   8/1998

OTHER PUBLICATIONS

Rhoads et al. Regulation of the cyanide–resistant alternative oxidase of plant mitochondria. J. Biol. Chem., Nov. 1998, Vo 273, No. 46, pp. 30750–30756.*

Haseloff, Jim, et al., *Removal of a cryptic intron and subcellular localization of green fluorescent protein are required to mark transgenic Arabidopsis plants brightly*, Proc. Natl. Acad. Sci. USA, vol. 94, pp. 2122–2127 (Mar. 1997).

Abstract, Wyatt, W. E., et al., *Effects of altered expression of the calcium–binding protein calreticulin in Arabidopsis thaliana*, Abstract XP–002185046 (Oct. 7, 1999).

International Search Report, International Application No. PCT/US01/13563 dated Dec. 28, 2001.

* cited by examiner

*Primary Examiner*—David T. Fox
*Assistant Examiner*—Cynthia Collins
(74) *Attorney, Agent, or Firm*—Myers Bigel Sibley & Sajovec, P.A.

(57) ABSTRACT

The present invention provides transgenic plants over-expressing a transgene encoding a calcium-binding protein or peptide (CaBP). Preferably, the CaBP is a calcium storage protein and over-expression thereof does not have undue adverse effects on calcium homeostasis or biochemical pathways that are regulated by calcium. In preferred embodiments, the CaBP is calreticulin (CRT) or calsequestrin. In more preferred embodiments, the CaBP is the C-domain of CRT, a fragment of the C-domain, or multimers of the foregoing. In other preferred embodiments, the CaBP is localized to the endoplasmic reticulum by operatively associating the transgene encoding the CaBP with an endoplasmic reticulum localization peptide. Alternatively, the CaBP is targeted to any other sub-cellular compartment that permits the calcium to be stored in a form that is biologically available to the plant. Also provided are methods of producing plants with desirable phenotypic traits by transformation of the plant with a transgene encoding a CaBP. Such phenotypic traits include increased calcium storage, enhanced resistance to calcium-limiting conditions, enhanced growth and viability, increased disease and stress resistance, enhanced flower and fruit production, reduced senescence, and a decreased need for fertilizer production. Further provided are plants with enhanced nutritional value as human food or animal feed.

22 Claims, 14 Drawing Sheets

(6 of 14 Drawing Sheet(s) Filed in Color)

```
   1 GAATTCGGCA CGAGCACGAC CTTAGGGGTT CAGATCGGAT CGGAAGCTTC
  51 CATAAGTTTC CATCGGGCGT CGCCGGTATG GCGATCCGCA AGGGGTCTTC
 101 GTACGCCGTC GCGGCACTTC TCGCGCTCGC CTCTGTCGCC GCCGTCGCAG
 151 GGGAGGTCTT CTTCCAGGAG AAGTTCGAAG ATGGCTGGGA AGTCGGTGG
 201 GTCAAGTCCG AGTGGAAGAA GGATGAGAAC ATGGCTGGTG AATGGAACCA
 251 CACATCTGGA AAATGGAATG GAGATGCCGA GGACAAAGGT ATTCAAACCT
 301 CCGAGGATTA CAGGTTCTAT GCCATTTCAG CCGAATACCC TGAGTTCAGC
 351 AACAAGGATA AGACCCTGGT GCTGCAGTTC TCTGTGAAGC ACGAGCAGAA
 401 GCTTGACTGC GGCGGTGGCT ACGTCAAGTT GCTGGGTGGT GATGTAGACC
 451 AGAAGACATT AGGTGGAGAC ACATCTTACA GCATTATCTC TCGCCCAGAT
 501 ATCTCTCGGT ACAGCACCAA GAAGGTTCAC ACTATCCTGA CCAAGGATGG
 551 CAAAAACCAC TTGATCAAGA AGGATGTCCC TTGTCAGACT GATCAGTTGA
 601 CTCATGTTTA CACTTTCATC ATCCGTCCTG ATGCAACATA CAGCATTCTC
 651 ATTGATAATG AAGAGAAGCA TACTGGCAGC ATCTACGAGC ATTGGGATAT
 701 TCTTCCCCCT AAGAAAATCA AGGACCCAGA GGCTAAGAAG CCTGAGGACT
 751 GGGATGACAA GGAGTACATT CCTGACCCTG AGGACAAGAA GCCAGAGGGC
 801 TATGATGATA TTCCCAAGGA AATTCCTGAC CCTGATGCTA AGAAGCCTGA
 851 GGACTGGGAC GATGAGGAAG ATGGTGAATG GACTGCCCCT ACCATTCCCA
 901 ACCCAGAATA CAAGGGACCA TGGAAACAAA AGAAAATCAA GAACCCGAAC
 951 TACCAGGGTA AATGGAAGGC ACCTATGATT GACAACCCAG ATTTTAAGGA
1001 TGATCCATAC ATTTACGCCT TCGACAGCTT GAAGTACATT GGCATTGAGC
1051 TGTGGCAGGT TAAATCGGGC ACTCTGTTCG ACAACATCAT CATCACTGAT
1101 GACCCTGCGT TGGCCAAGAC TTTTGCAGAG GAGACCTGGG GCAAGCACAA
1151 GGAGGCAGAA AAGGCTGCTT TTGATGAGGC CGAGAAAAAG AAGGAAGAAG
1201 AGGATGCCGC CAAGGGTGGG GATGATGAGG ATGATGACCT AGAGGATGAG
1251 GAAGACGATG AGAAGGCAGA CGAGGACAAG GCCGACTCTG ATGCCGAGGA
1301 TGGCAAGGAT TCTGATGATG AGAAGCACGA CGAGCTCTAG ATGGCGAGGA
1351 TGATGTTGCT GGCCTAGATT TATCAGCTCT GCCACTATGA AGTTCTTTTT
1401 TTTTTCCCGT GACCATCAAG AAGTAGAACA CTGCTAATAA GCAGATGGAC
1451 AGTTTGGGTC GCCGTAGCGC TTTGTAGTCA TTTTTCCCAT TAAAGCCGAT
1501 AACACTGAAC AAGGAGGAAG GATCTTTTGC CAAAAAAAAA AAAAA
```

*FIG. 1*

```
     At  .......... ..........  NSARASAAVI FEERFDD.GW ENRWVKSEWK KDDNTAGEWK
     Np  MATQRRANPS SLHLITVFSL  LVAVVSAEVF FEESFND.GW ESRWVKSEWK KDENMAGEWN
     Zm  ..MAIRKGSS YAVAALLALA  SVAAVAGEVF FQEKFED.GW ESRWVKSEWK KDENMAGEWN
     Dm  ........MM WCKTVIVLLA  TVGFISAEVY LKENFDNENW EDTWIYS..K HPGKEFGKFV
     Bt  .MCLNHFLLS LVLSIVLLFH  FVFYICL... ..HHIVTFLR EETVFFS..E QFLTLDLKYK 61                                                          120
     At  HTAGNWSGDA .NDKGIQTSE  DYRFYAISAE FPEFSNKDKT LVFQFS..VK HEQKLDCGGG
     Np  HTSGKWNGDA .NDKGIQTSE  DYRFYAISAE FPEFSNKGKN LVFQFS..VK HEQKLDCGGG
     Zm  HTSGKWNGDA .EDKGIQTSE  DYRFYAISAE YPEFSNKDKT LVLQFS..VK HEQKLDCGGG
     Dm  LTPGTFYNDA EADKGIQTSQ  DARFYAASRK FDGFSNEDKP LVVQFS..VK HEQNIDCGGG
     Bt  ASKLSSIREA LSMSKVGIIE  NFCFSEISFL QESIKSHGRR TLVGCSPWGH EEQNIDCGGG 121                                                         180
     At  YMKLLSGDVD QKKFGGDTPY  SIMFGPDICG YSTKKVHAIL TYNGANHLIK KDVPCETDQL
     Np  YMKLLSGDVD QKKFGGDTPY  SIMFGPDICG YSTKKVHAIL TYNDTNHLIK KEVPCETDQL
     Zm  YVKLLGGDVD QKTLGGDTSY  SIISRPDISR YSTKKVHTIL TKDGKNHLIK KDVPCQTDQL
     Dm  YVKLFDCSLD QTDMHGESPY  EIMFGPDICG PGTKKVHVIF SYKGKNHLIS KDIRCKDDVY
     Bt  YVNVFPAGLD QTDMHGDSEY  NIMFGPDICG PGTKKVHVIF NYKGKNVLIN KDIRCKDDEF 181                                                         240
     At  THVYTFILRP DATYSILIDN  VEKQTGSLYS DWDLLPPKKI KDPSAKKPED WDEQEYISDP
     Np  THVYTFILRP DATYSILIDN  VEKQSGSLYS DWDLLPPKTI KDPSAKKPED WDEKEFIDDP
     Zm  THVYTFIIRP DATYSILIDN  EEKHTGSIYE HWDILPPKKI KDPEAKKPED WDDKEYIPDP
     Dm  THFYTLIVRP DNTYEVLIDN  EKVESGNLED DWDFLAPKKI KDPTATKPED WDDRATIPDP
     Bt  THLYTLIVRP NNTYEVKIDN  SQVESGSLED DWDFLPPKKI KDPDAAKPED WDDRAKIDDP 241                                                         300
     At  EDKKTDGYDD IPKEIPDTDS  KKPEDWDDEE DGEWTAPTIP NPEYMGEWKP KQIKNPNYKG
     Np  EDKKPEGYDD IPEEITDPDA  KKPEDWDDEE DGEWTAPTIP NPEYKGPWKP KKIKNPNYKG
     Zm  EDKKPEGYDD IPKEIPDPDA  KKPEDWDDEE DGEWTAPTIP NPEYKGPWKQ KKIKNPNYQG
     Dm  DDKKPEDWDK .PEHIPDPDA  TKPEDWDDEM DGEWEPPMID NPEFKGEWQP KQLDNPNYKG
     Bt  TDSKPEDWDK .PEHIPDPDA  KKPEDWDEEM DGEWEPPLIQ NPEYKGEWKP RQIDNPEYKG

301  ──C-DOMAIN──▶                                          360
     At  KWEAPLIDNP DFKDDPELYV  FPKLKYVGLE LWQVKSGSLF DNVLICDDPD YAKKLADETW
     Np  KWKAPLIDNP DFKDDPDLYV  FPKLKYVGVE LWQVKSGTLF DNIVICDDPE YAKAIAEETW
     Zm  KWKAPMIDNP DFKDDPYIYA  FDSLKYIGIE LWQVKSGTLF DNIIITDDPA LAKTFAEETW
     Dm  AWEHPEIANP EYVPDDKLYL  RKEICTLGFD LWQVKSGTIF DNVLITDDVE LAAKAAAEVK
     Bt  IWIHPEIDNP EYSPDSNIYA  YENFAVLGLD LWQVKSGTIF DNFLITNDEA YAEEFGNETW 361                                                         420
     At  GKLKDAE... KAAFDEAEKK  NEEEE.SKDA PAESDAEDEP EDDEGGDDSD SESKAEETKS
     Np  GKQKDAE... KAAFEEAEKK  REEEE.SKAA PADSDAEEDD DADDDSDDAD DKSES.....
     Zm  GKHKEAE... KAAFDEAEKK  KEEEDAAKGG DDEDDDLEDE EDDEKADEDK ADSDAEDGKD
     Dm  N.TQAGEKKM KEAQDEVQRK  KDEEEAKKAS DKDDEDEDDD DEEKDDESKQ DKDQSE....
     Bt  GVTKAAEKQM KDKQDEEQRL  HEEEEEKKGK EEEEAEKDDD EDKDEDEEDE DEKEEEEEED 421         437
     At  EDSEETSEKD ATAHDEL
     Np  ........KD DEAHDEL
     Zm  SD......D  EK.HDEL
     Dm  .......... ...HDEL
     Bt  AAAA...... .QAKDEL
```

*FIG. 2*

```
CCT ATG ATT GAC AAC CCA GAT TTT AAG GAT GAT CCA TAC
 P   M   I   D   N   P   D   F   K   D   D   P   Y
ATT TAC GCC TTC GAC AGC TTG AAG TAC ATT GGC ATT GAG
 I   Y   A   F   D   S   L   K   Y   I   G   I   E
CTG TGG CAG GTT AAA TCG GGC ACT CTG TTC GAC AAC ATC
 L   W   Q   V   K   S   G   T   L   F   D   N   I
ATC ATC ACT GAT GAC CCT GCG TTG GCC AAG ACT TTT GCA
 I   I   T   D   D   P   A   L   A   K   T   F   A
GAG GAG ACC TGG GGC AAG CAC AAG GAG GCA GAA AAG GCT
 E   E   T   W   G   K   H   K   E   A   E   K   A
GCT TTT GAT GAG GCC GAG AAA AAG AAG GAA GAA GAG GAT
 A   F   D   E   A   E   K   K   K   E   E   E   D
GCC GCC AAG GGT GGG GAT GAT GAG GAT GAT GAC CTA GAG
 A   A   K   G   G   D   D   E   D   D   D   L   E
GAT GAG GAA GAC GAT GAG AAG GCA GAC GAG GAC AAG GCC
 D   E   E   D   D   E   K   A   D   E   D   K   A
GAC TCT GAT GCC GAG GAT GGC AAG GAT TCT GAT GAT GAG
 D   S   D   A   E   D   G   K   D   S   D   D   E
AAG CAC GAC GAG CTC TAG
 K   H   D   E   L   *
```

*FIG. 4*

CRT
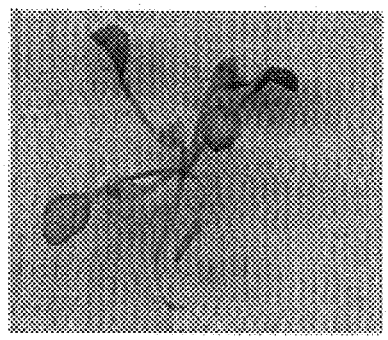 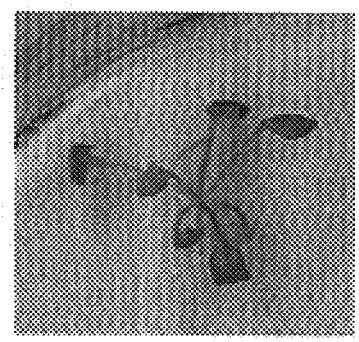
HS     −     +
Prot. Ex. 
*FIG. 6*

150 mM NaCl

200 Mm NaCl, 12 DAYS

SEQUENCE LISTING

```
<160> NUMBER OF SEQ ID NOS: 8

<210> SEQ ID NO 1
<211> LENGTH: 1545
<212> TYPE: DNA
<213> ORGANISM: Zea mays
<220> FEATURE:
<221> NAME/KEY: CDS
```

-continued

<210> LOCATION: (78)..(1340)

<400> SEQUENCE: 1

```
gaattcggca cgagcacgac cttaggggtt cagatcggat cggaagcttc cataagtttc      60
catcgggcgt cgccggt atg gcg atc cgc aag ggg tct tcg tac gcc gtc       110
                   Met Ala Ile Arg Lys Gly Ser Ser Tyr Ala Val
                    1               5                  10 gcg gca ctt ctc gcg ctc gcc tct gtc gcc gcc gtc gca ggg gag gtc      158
Ala Ala Leu Leu Ala Leu Ala Ser Val Ala Ala Val Ala Gly Glu Val
             15                  20                  25 ttc ttc cag gag aag ttc gaa gat ggc tgg gaa agt cgg tgg gtc aag      206
Phe Phe Gln Glu Lys Phe Glu Asp Gly Trp Glu Ser Arg Trp Val Lys
         30                  35                  40 tcc gag tgg aag aag gat gag aac atg gct ggt gaa tgg aac cac aca      254
Ser Glu Trp Lys Lys Asp Glu Asn Met Ala Gly Glu Trp Asn His Thr
     45                  50                  55 tct gga aaa tgg aat gga gat gcc gag gac aaa ggt att caa acc tcc      302
Ser Gly Lys Trp Asn Gly Asp Ala Glu Asp Lys Gly Ile Gln Thr Ser
 60                  65                  70                  75 gag gat tac agg ttc tat gcc att tca gcc gaa tac cct gag ttc agc      350
Glu Asp Tyr Arg Phe Tyr Ala Ile Ser Ala Glu Tyr Pro Glu Phe Ser
                 80                  85                  90 aac aag gat aag acc ctg gtg ctg cag ttc tct gtg aag cac gag cag      398
Asn Lys Asp Lys Thr Leu Val Leu Gln Phe Ser Val Lys His Glu Gln
             95                 100                 105 aag ctt gac tgc ggc ggt ggc tac gtc aag ttg ctg ggt ggt gat gta      446
Lys Leu Asp Cys Gly Gly Gly Tyr Val Lys Leu Leu Gly Gly Asp Val
        110                 115                 120 gac cag aag aca tta ggt gga gac aca tct tac agc att atc tct cgc      494
Asp Gln Lys Thr Leu Gly Gly Asp Thr Ser Tyr Ser Ile Ile Ser Arg
    125                 130                 135 cca gat atc tct cgg tac agc acc aag aag gtt cac act atc ctg acc      542
Pro Asp Ile Ser Arg Tyr Ser Thr Lys Lys Val His Thr Ile Leu Thr
140                 145                 150                 155 aag gat ggc aaa aac cac ttg atc aag aag gat gtc cct tgt cag act      590
Lys Asp Gly Lys Asn His Leu Ile Lys Lys Asp Val Pro Cys Gln Thr
                160                 165                 170 gat cag ttg act cat gtt tac act ttc atc atc cgt cct gat gca aca      638
Asp Gln Leu Thr His Val Tyr Thr Phe Ile Ile Arg Pro Asp Ala Thr
            175                 180                 185 tac agc att ctc att gat aat gaa gag aag cat act ggc agc atc tac      686
Tyr Ser Ile Leu Ile Asp Asn Glu Glu Lys His Thr Gly Ser Ile Tyr
        190                 195                 200 gag cat tgg gat att ctt ccc cct aag aaa atc aag gac cca gag gct      734
Glu His Trp Asp Ile Leu Pro Pro Lys Lys Ile Lys Asp Pro Glu Ala
    205                 210                 215 aag aag cct gag gac tgg gat gac aag gag tac att cct gac cct gag      782
Lys Lys Pro Glu Asp Trp Asp Asp Lys Glu Tyr Ile Pro Asp Pro Glu
220                 225                 230                 235 gac aag aag cca gag ggc tat gat gat att ccc aag gaa att cct gac      830
Asp Lys Lys Pro Glu Gly Tyr Asp Asp Ile Pro Lys Glu Ile Pro Asp
                240                 245                 250 cct gat gct aag aag cct gag gac tgg gac gat gag gaa gat ggt gaa      878
Pro Asp Ala Lys Lys Pro Glu Asp Trp Asp Asp Glu Glu Asp Gly Glu
            255                 260                 265 tgg act gcc cct acc att ccc aac cca gaa tac aag gga cca tgg aaa      926
Trp Thr Ala Pro Thr Ile Pro Asn Pro Glu Tyr Lys Gly Pro Trp Lys
        270                 275                 280 caa aag aaa atc aag aac ccg aac tac cag ggt aaa tgg aag gca cct      974
```

-continued

```
Gln Lys Lys Ile Lys Asn Pro Asn Tyr Gln Gly Lys Trp Lys Ala Pro
    285                 290                 295 atg att gac aac cca gat ttt aag gat gat cca tac att tac gcc ttc      1022
Met Ile Asp Asn Pro Asp Phe Lys Asp Asp Pro Tyr Ile Tyr Ala Phe
300                 305                 310                 315 gac agc ttg aag tac att ggc att gag ctg tgg cag gtt aaa tcg ggc      1070
Asp Ser Leu Lys Tyr Ile Gly Ile Glu Leu Trp Gln Val Lys Ser Gly
                320                 325                 330 act ctg ttc gac aac atc atc atc act gat gac cct gcg ttg gcc aag      1118
Thr Leu Phe Asp Asn Ile Ile Ile Thr Asp Asp Pro Ala Leu Ala Lys
            335                 340                 345 act ttt gca gag gag acc tgg ggc aag cac aag gag gca gaa aag gct      1166
Thr Phe Ala Glu Glu Thr Trp Gly Lys His Lys Glu Ala Glu Lys Ala
        350                 355                 360 gct ttt gat gag gcc gag aaa aag aag gaa gaa gag gat gcc gcc aag      1214
Ala Phe Asp Glu Ala Glu Lys Lys Lys Glu Glu Glu Asp Ala Ala Lys
    365                 370                 375 ggt ggg gat gat gag gat gat gac cta gag gat gag gaa gac gat gag      1262
Gly Gly Asp Asp Glu Asp Asp Asp Leu Glu Asp Glu Glu Asp Asp Glu
380                 385                 390                 395 aag gca gac gag gac aag gcc gac tct gat gcc gag gat ggc aag gat      1310
Lys Ala Asp Glu Asp Lys Ala Asp Ser Asp Ala Glu Asp Gly Lys Asp
                400                 405                 410 tct gat gat gag aag cac gac gag ctc tag atggcgagga tgatgttgct        1360
Ser Asp Asp Glu Lys His Asp Glu Leu
            415                 420 ggcctagatt tatcagctct gccactatga agttctttt ttttccccgt gaccatcaag     1420
aagtagaaca ctgctaataa gcagatggac agtttgggtc gccgtagcgc tttgtagtca    1480
ttttccccat taaagccgat aacactgaac aaggaggaag gatctttttgc caaaaaaaaa    1540 aaaaa                                                                 1545

<210> SEQ ID NO 2
<211> LENGTH: 420
<212> TYPE: PRT
<213> ORGANISM: Zea mays

<400> SEQUENCE: 2

Met Ala Ile Arg Lys Gly Ser Ser Tyr Ala Val Ala Leu Leu Ala
1               5                   10                  15

Leu Ala Ser Val Ala Ala Val Ala Gly Glu Val Phe Phe Gln Glu Lys
                20                  25                  30

Phe Glu Asp Gly Trp Glu Ser Arg Trp Val Lys Ser Glu Trp Lys Lys
            35                  40                  45

Asp Glu Asn Met Ala Gly Glu Trp Asn His Thr Ser Gly Lys Trp Asn
        50                  55                  60

Gly Asp Ala Glu Asp Lys Gly Ile Gln Thr Ser Glu Asp Tyr Arg Phe
65                  70                  75                  80

Tyr Ala Ile Ser Ala Glu Tyr Pro Glu Phe Ser Asn Lys Asp Lys Thr
                85                  90                  95

Leu Val Leu Gln Phe Ser Val Lys His Glu Gln Lys Leu Asp Cys Gly
            100                 105                 110

Gly Gly Tyr Val Lys Leu Leu Gly Gly Asp Val Asp Gln Lys Thr Leu
        115                 120                 125

Gly Gly Asp Thr Ser Tyr Ser Ile Ile Ser Arg Pro Asp Ile Ser Arg
    130                 135                 140
```

-continued

```
Tyr Ser Thr Lys Lys Val His Thr Ile Leu Thr Lys Asp Gly Lys Asn
145                 150                 155                 160

His Leu Ile Lys Lys Asp Val Pro Cys Gln Thr Asp Gln Leu Thr His
            165                 170                 175

Val Tyr Thr Phe Ile Ile Arg Pro Asp Ala Thr Tyr Ser Ile Leu Ile
        180                 185                 190

Asp Asn Glu Glu Lys His Thr Gly Ser Ile Tyr Glu His Trp Asp Ile
    195                 200                 205

Leu Pro Pro Lys Lys Ile Lys Asp Pro Glu Ala Lys Lys Pro Glu Asp
210                 215                 220

Trp Asp Asp Lys Glu Tyr Ile Pro Asp Pro Glu Asp Lys Lys Pro Glu
225                 230                 235                 240

Gly Tyr Asp Asp Ile Pro Lys Glu Ile Pro Asp Pro Asp Ala Lys Lys
                245                 250                 255

Pro Glu Asp Trp Asp Asp Glu Glu Asp Gly Glu Trp Thr Ala Pro Thr
                260                 265                 270

Ile Pro Asn Pro Glu Tyr Lys Gly Pro Trp Lys Gln Lys Lys Ile Lys
        275                 280                 285

Asn Pro Asn Tyr Gln Gly Lys Trp Lys Ala Pro Met Ile Asp Asn Pro
    290                 295                 300

Asp Phe Lys Asp Asp Pro Tyr Ile Tyr Ala Phe Asp Ser Leu Lys Tyr
305                 310                 315                 320

Ile Gly Ile Glu Leu Trp Gln Val Lys Ser Gly Thr Leu Phe Asp Asn
                325                 330                 335

Ile Ile Ile Thr Asp Asp Pro Ala Leu Ala Lys Thr Phe Ala Glu Glu
                340                 345                 350

Thr Trp Gly Lys His Lys Glu Ala Glu Lys Ala Ala Phe Asp Glu Ala
        355                 360                 365

Glu Lys Lys Lys Glu Glu Glu Asp Ala Ala Lys Gly Gly Asp Asp Glu
    370                 375                 380

Asp Asp Asp Leu Glu Asp Glu Glu Asp Asp Glu Lys Ala Asp Glu Asp
385                 390                 395                 400

Lys Ala Asp Ser Asp Ala Glu Asp Gly Lys Asp Ser Asp Asp Glu Lys
                405                 410                 415

His Asp Glu Leu
        420
```

<210> SEQ ID NO 3
<211> LENGTH: 28
<212> TYPE: DNA
<213> ORGANISM: Artificial Sequence
<220> FEATURE:
<221> NAME/KEY: misc_feature
<222> LOCATION: (1)..(28)
<223> OTHER INFORMATION: Synthetic Oligonucleotide.

<400> SEQUENCE: 3
gctctagaat gaagactaat cttttct                              28

<210> SEQ ID NO 4
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic Oligonucleotide.

<400> SEQUENCE: 4

```
gcatgctgtt tgtatagttc atcc                                              24
```

<210> SEQ ID NO 5
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic Oligonucleotide.

<400> SEQUENCE: 5

```
acatgcatgc ccctatgttg acaacc                                            26
```

<210> SEQ ID NO 6
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic Oligonucleotide.

<400> SEQUENCE: 6

```
acatgcatgc cgatctagag ctcgtc                                            26
```

<210> SEQ ID NO 7
<211> LENGTH: 369
<212> TYPE: DNA
<213> ORGANISM: Zea mays
<220> FEATURE:
<221> NAME/KEY: CDS
<222> LOCATION: (1)..(369)

<400> SEQUENCE: 7

```
cct atg att gac aac cca gat ttt aag gat gat cca tac att tac gcc        48
Pro Met Ile Asp Asn Pro Asp Phe Lys Asp Asp Pro Tyr Ile Tyr Ala
1               5                   10                  15 ttc gac agc ttg aag tac att ggc att gag ctg tgg cag gtt aaa tcg        96
Phe Asp Ser Leu Lys Tyr Ile Gly Ile Glu Leu Trp Gln Val Lys Ser
            20                  25                  30 ggc act ctg ttc gac aac atc atc atc act gat gac cct gcg ttg gcc       144
Gly Thr Leu Phe Asp Asn Ile Ile Ile Thr Asp Asp Pro Ala Leu Ala
        35                  40                  45 aag act ttt gca gag gag acc tgg ggc aag cac aag gag gca gaa aag       192
Lys Thr Phe Ala Glu Glu Thr Trp Gly Lys His Lys Glu Ala Glu Lys
    50                  55                  60 gct gct ttt gat gag gcc gag aaa aag aag gaa gaa gag gat gcc gcc       240
Ala Ala Phe Asp Glu Ala Glu Lys Lys Lys Glu Glu Glu Asp Ala Ala
65                  70                  75                  80 aag ggt ggg gat gat gag gat gat gac cta gag gat gag gaa gac gat       288
Lys Gly Gly Asp Asp Glu Asp Asp Asp Leu Glu Asp Glu Glu Asp Asp
                85                  90                  95 gag aag gca gac gag gac aag gcc gac tct gat gcc gag gat ggc aag       336
Glu Lys Ala Asp Glu Asp Lys Ala Asp Ser Asp Ala Glu Asp Gly Lys
            100                 105                 110 gat tct gat gat gag aag cac gac gag ctc tag                           369
Asp Ser Asp Asp Glu Lys His Asp Glu Leu
        115                 120
```

<210> SEQ ID NO 8
<211> LENGTH: 122
<212> TYPE: PRT
<213> ORGANISM: Zea mays

```
<400> SEQUENCE: 8

Pro Met Ile Asp Asn Pro Asp Phe Lys Asp Asp Pro Tyr Ile Tyr Ala
1               5                   10                  15

Phe Asp Ser Leu Lys Tyr Ile Gly Ile Glu Leu Trp Gln Val Lys Ser
            20                  25                  30

Gly Thr Leu Phe Asp Asn Ile Ile Ile Thr Asp Asp Pro Ala Leu Ala
            35                  40                  45

Lys Thr Phe Ala Glu Glu Thr Trp Gly Lys His Lys Glu Ala Glu Lys
        50                  55                  60

Ala Ala Phe Asp Glu Ala Glu Lys Lys Lys Glu Glu Glu Asp Ala Ala
65                  70                  75                  80

Lys Gly Gly Asp Asp Glu Asp Asp Asp Leu Glu Asp Glu Glu Asp Asp
            85                  90                  95

Glu Lys Ala Asp Glu Asp Lys Ala Asp Ser Asp Ala Glu Asp Gly Lys
            100                 105                 110

Asp Ser Asp Asp Glu Lys His Asp Glu Leu
        115                 120
```

TRANSGENIC PLANTS WITH INCREASED CALCIUM STORES

RELATED APPLICATIONS

This application claims the benefit of U.S. provisional application serial No. 60/200,233, filed Apr. 28, 2000, the disclosure of which is incorporated by reference herein in its entirety.

STATEMENT OF FEDERAL SUPPORT

This invention was made with government support under grant number NAGW-4984 from NASA. The federal government has certain rights to this invention.

FIELD OF THE INVENTION

The present invention relates to transgenic plants, in particular, the present invention relates to transgenic plants expressing a calcium-binding protein that increases available calcium stores in the plant.

BACKGROUND OF THE INVENTION

Calcium plays an essential role in plant growth and development and is involved in multiple signal transduction pathways. Whereas cytoplasmic calcium concentrations are tightly regulated, higher levels of calcium are found in subcellular organelles (Gilroy et al., (1993) *J. Cell Science* 106:453). Modulation of cytoplasmic calcium levels provides a rapid response to environmental stimuli and is achieved by a system of $Ca^{2+}$-transport and storage pathways that include $Ca^{2+}$ buffering proteins in the lumen of intracellular compartments. The endoplasmic reticulum (ER), cell wall, and the vacuole contain high levels of calcium that could be released to the cytoplasm. Unlike animal cells, the majority of $Ca^{2+}$ in plant cells is found in the cell wall and vacuole, not in the ER (Bush, (1995) *Ann. Review Plant Physiol Plant Molec. Biol.* 46:95). Except for the vacuole, which may not readily release calcium (Hirschi et al., (1999) *Plant Cell* 11:2113), the availability of these stores for signaling has not been demonstrated. A voltage-gated, calcium-release channel has been identified in the endoplasmic reticulum (ER) of plants (Klusener et al., (1995) *EMBO J.* 14:2708). This channel is responsive to mechanotransduction, suggesting that the ER calcium store may be an important component of signal transduction pathways in plants as well as animals (Klusener et al., (1995) *EMBO J.* 14:2708). In plants, the major $Ca^{2+}$ storage protein in the ER is calreticulin (CRT) (Hassan et al., (1995) *Biochem. Biophys. Res. Commun.* 211:54; Navazio et al., (1998) *Plant Physiol.* 109:983).

$Ca^{2+}$ has long been recognized as an important second messenger responsible for mediating the activities of many environmental and endogenous signals. Cytosolic $Ca^{2+}$ concentrations often show significant changes in plant cells under the influence of various stress signals such as touch, cold or heat shock, wounding, anoxia, salinity, and hypoosmotic shock (Knight et al., (1991) *Nature* 352:524; Knight et al., (1992) *Proc. Nat. Acad. Sci. USA* 89:4967; Knight et al., (1996) *Plant Cell* 8:489; Haley et al., (1995) *Proc. Nat Acad. Sci. USA* 92:4124; Campbell et al., (1996) *Cell Calcium* 19:211; Polisensky and Braam, (1996) *Plant Physiol.* 11:1271; Subbaian et al., (1994) *Plant Physiol.* 105:369; Lynch et al., (1989) *Plant Physiol.* 90:1271; Bush, (1996) *Planta* 199:89; Okazaki et al., (1996) *Plant, Cell and Environment* 19:569; Takahashi et al., (1997) *Plant Physiol.* 113:587). A stress-induced change in cytoplasmic calcium concentrations may be one of the primary transduction mechanisms whereby gene expression and biochemical events are altered to adapt plant cells to environmental stresses (Monroy et al., (1993) *Plant Physiol.* 102:1227; Subbaiah et al., (1994) *Plant Physiol.* 105: 369; Monroy and Dhindsa, (1995) *Plant Cell* 7:321; Braam et al., (1996) *Physiol. Plant* 98:909).

A variety of plant diseases and growth disorders causing substantial losses to horticultural crops have been attributed to calcium deficiency. Color breakdown in Anthurium spathes (Higaki et al., (1980) *J. Am. Soc. Hortic. Sci.* 105;438; Higaki et al., (1980) *J. Am. Soc. Hortic. Sci.* 105:441) can result in field losses of 50% and losses after shipments of up to 20%. Other conditions include but are not limited to tipburn in lettuce, cabbage and cauliflower (Goto & Takakura, (1992) *Trans. Am. Soc. Ag. Engineers* 35;641; Barta & Tibbitts, (1986) *J. Am. Soc. Hortic. Sci.* 111:413; Aloni, (1986) *J. Hortic. Sci.* 61:509; Maynard et al., (1981) *Hotsci.* 16:193), shoot-tip necrosis in potatoes, a physiological disorder found in normal microculture conditions, that makes the cultures useless for micropropagation or research (Sha et al., (1985) *J. Am. Soc. Hortic. Sci.* 110:631); and blossom end rot in tomato (DeKock et al., (1980) *J. Sci. Food Agric.* 33:509; Banuelos et al., (1985) *Am. Soc. Hortic. Sci.* 20:894; Ho & Adams, (1994) *J. Hortic. Sci.* 69:367). Addition of $CaCO_3$ does not remedy the problem in areas where additional factors such as soil salinity and pH are sub-optimal (Bower & Turk, (1946) *J. Am. Soc. Agron.* 38:723; McLaughlin et al., (1993) *Can. J. For. Res. Rev. Can. Rech. For.* 23:380; McCray et al., (1991) *Soil Use Manage* 7:193; Francois et al., (1991) *Hort. Science* 26:549) or where the condition results from localized deficiencies caused by uneven $Ca^{2+}$ distribution in tissues (Francois, et al, (1991) *Hort. Science* 26:549; Ho & Adams, (1994) *J. Hortic. Sci.* 69:367). Deficiencies may be exaggerated by high transpiration rates in a desert environment or a reduction in root pressure resulting from soil salinity (Francois, et al, (1991) *Hort. Science* 26:549; Ho & Adams, (1994) *J. Hortic. Sci.* 69:367). A temporary calcium deficiency of 8–10 days resulted in reduced stem growth and death of the apical meristem in tomato (Morand et al., (1996) *J. Plant Nutr.* 19:115).

Calreticulin is a multifunctional calcium-binding protein that is highly conserved in eukaryotic cells (Michalak et al. (1998) *Biochem. Cell. Biol.* 76:779; Michalak et al., (1999) *Biochem. J.* 344 Pt. 2:281; Dresselhaus et al., (1996) *Plant Molec. Biol.* 31:23; Krause & Michalak, (1997) *Cell* 88:439). The conservation of CRT and the fact that CRT knockouts are lethal in mice (Mesaeli et al., (1999) *J. Cell. Biol.* 144:857) suggest that CRT performs an essential function. In plants, CRT has been localized to the endoplasmic reticulum, Golgi, plasmodesmata, and plasma membrane (Borisjuk et al., (1998) *Planta* 206:504; Hassan et al. (1995) *Biochem. Biophys. Res. Commun.* 211:54; Baluska et al., (1999) *Plant J.* 19:481). The protein includes a signal sequence and ER retention motif for ER localization, and also has a nuclear localization sequence. Although these localization sequences appear to be conserved across species, there is contradictory evidence for nuclear localization.

CRT has been shown to function as a chaperone in the ER (Peterson & Helenius, (1999) *J. Cell. Sci.* 112:2775; Saito et al., (1999) *EMBO J.* 18:6718; Denecke et al., (1995) *Plant Cell* 7:391; Nauseef et al., (1995) *J. Biol. Chem.* 270:4741; Qtteken & Moss, (1996) *J. Biol. Chem.* 271:97; Crofts & Denecke, (1998) *Trends Plant Sci.* 3:396). Other proposed roles include regulation of gene expression (Perrone et al.

(1999) *J. Biol. Chem.* 274:4640; signaling (Rauch et al., (2000) *Exp. Cell Res.* 256:105), and serving as a calcium buffer (Mesaeli et al., (1999) *J. Cell. Biol.* 144:857). In animal cells, calreticulin mRNA decreases during calcium depletion, along with resting and IP3-sensitive calcium pools (Mailhot et al., (2000) *Endocrinology* 141:891). Persson et al. (in press) demonstrates that altered expression of calreticulin (CRT) altered Ca2+ uptake and release in ER-enriched membrane fractions. The data indicate that the pool of Ca2+ in the ER can be affected by altering expression of CRT.

CRT has three functional domains: a globular N-domain, a proline rich, high affinity, low capacity $Ca^{2+}$-binding domain (the P-domain) and a highly acidic, low affinity, high capacity $Ca^{2+}$-binding domain (the C-domain) (Michalak et al., (1992) *Biochem. J.* 285:681). The P-domain shares considerable homology with the ER chaperone calnexin, which is also found in plants and functions as a chaperone. In addition, in Xenopus oocytes the P-domain has been implicated as the active region in $Ca^{2+}$ signal transduction (Camacho & Lechleiter, (1995) *Cell* 82:765). The C-domain is a highly acidic region that has been shown to bind 20–50 moles of $Ca^{2+}$/mole of protein and, thus, appears to be a major site of $Ca^{2+}$ storage within the ER (Michalak et al., (1992) *Biochem. J.* 285:681). Calsequestrin, a calcium-binding protein related to the C-domain of CRT, is not found in plants (Navazio et al., (1995) *J. Eukeryot. Microbiol.* 45:307).

Hirschi et al., (1999) *Plant Cell* 11:2113 over-expressed a tonoplast $Ca^{2+}/H^+$ antiporter (CAX) in Arabidopsis and tobacco. Plants transgenic for CAX had an increased need for calcium and showed a hightened sensitivity to cold when grown on normal medium. It appears that the introduction of the CAX transgene resulted in storage of calcium in a form that was not available to the plant, thereby producing a calcium-deficient state in the plant.

WO 98/36084 suggests transforming a plant with bovine intestinal calcium binding protein to increase calcium accumulation in the plant. However, this protein only binds 2 moles of calcium per mole of protein, and over-expression of this protein may have adverse consequences on calcium signaling and homeostasis in the plant. Further, it is unclear whether calcium bound to this protein would be in a biologically active form for the plant.

Accordingly, there is a need in the art for methods of improving available calcium stores in plants without unduly perturbing calcium homeostasis.

SUMMARY OF THE INVENTION

The present invention provides transgenic plants over-expressing a transgene encoding a calcium-binding protein or peptide (CaBP). Preferably, the CaBP is a calcium storage protein and over-expression does not have undue adverse effects on calcium homeostasis or biochemical pathways that are regulated by calcium. In preferred embodiments, the CaBP is calreticulin (CRT) or calsequestrin. In more preferred embodiments, the CaBP is the C-domain of CRT, a C-domain fragment, or multimers of the foregoing. In other preferred embodiments, the CaBP is localized to the endoplasmic reticulum by operatively associating the transgene encoding the CaBP with an endoplasmic reticulum localization signal peptide. Alternatively, the CaBP is targeted to any other sub-cellular compartment that permits the calcium to be stored in a form that is biologically available to the plant.

The inventive transgenic plants may have advantageous phenotypic traits as compared with wild-type plants. Increased calcium storage in the plants may result in an enhanced resistance (i.e., tolerance) to calcium-limiting conditions and/or improved stress resistance under such conditions. The plants of the invention may further have enhanced growth and viability, increased disease and stress resistance, enhanced flower and fruit production, reduced senescence, and a decreased need for fertilizer supplementation. Further, the plants of the invention may have an enhanced nutritional value (e.g., as a source of calcium) for use as human food or animal feed.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 1 is a cDNA sequence encoding a full-length maize calreticulin (SEQ ID NO:1).

FIG. 2 is an alignment of representative calreticulin sequences. A maize cDNA (SEQ ID NO:1) encoding the full-length CRT protein (SEQ ID NO:2) was obtained. Alignment with protein sequences of CRT from other species shows significant sequence homology across species, especially in the calcium binding domains. All include a signal sequence and H(K)DEL for ER localization and the three functional domains. The high affinity $Ca^{2+}$ binding sites of the P-domain are double-underlined, the putative nuclear localization signal is boxed, and the acidic residues of the high capacity/low affinity $Ca^{2+}$ binding C-domain are underlined. At=*Arabidopsis thaliana*, Nb=*Nicotiana plumbaginifolia*, Zm=*Zea mays*, Dm=*Drosophila melanogaster*, and Bt=*Bos taurus*.

FIG. 4 shows the nucleotide (SEQ ID NO:7) and amino acid (SEQ ID NO:8) sequences of a maize C-domain CRT fragment.

FIG. 6 shows the effects of heat shock on seedlings from a transgenic line of Arabidopsis, At2101-3, that over-expresses a CRT construct after heat shock, as shown by Western blot analysis.

Total protein was extracted from the seedlings, run on SDS-PAGE (2.5 mg tissue/lane), and transferred onto a nitrocellulose membrane. The membrane was probed with polyclonal antibodies against GFP. Lane 1, WT Arabidopsis; Lane 2, Arabidopsis expressing mGFP5 under the control of the Arabidopsis HS promoter (At2011); and Lane 3, Arabidopsis expressing GFP-CRT C-domain fusion protein under the control of the HS promoter (At2311-7).

Figure 9:
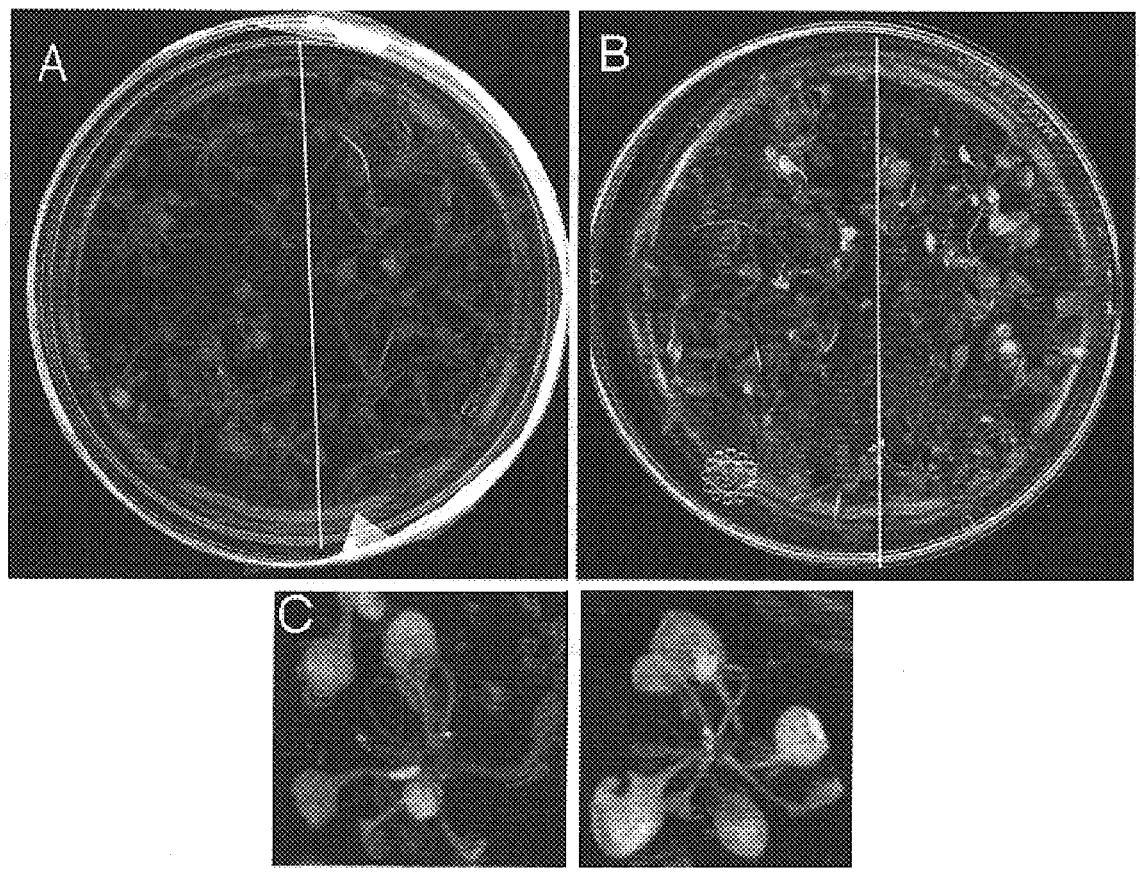

FIG. 9 presents photographs demonstrating altered expression of CRT C-domain alters viability of Arabidopsis seedlings on reduced calcium media. Seeds from At2311-7 (GFP-CRT C-domain overexpression) (left) and At2011 (GFP expressers) (right) were planted on nutrient media and allowed to germinate. Sixteen days after germination, seedlings were incubated at 35° C. for 2 hours (heat shock) and allowed to recover at 21° C. overnight. This is repeated on 3 consecutive days. On day 4, the plants were placed on fresh media containing 10 mM EGTA. Photographs shown were taken: Panel A) at time 0 and Panel B) 9 days after transfer to low calcium medium. Panel C) An individual seedling of each At2311 (left) and At2011 (right) 9 days after transfer.

Figure 10:
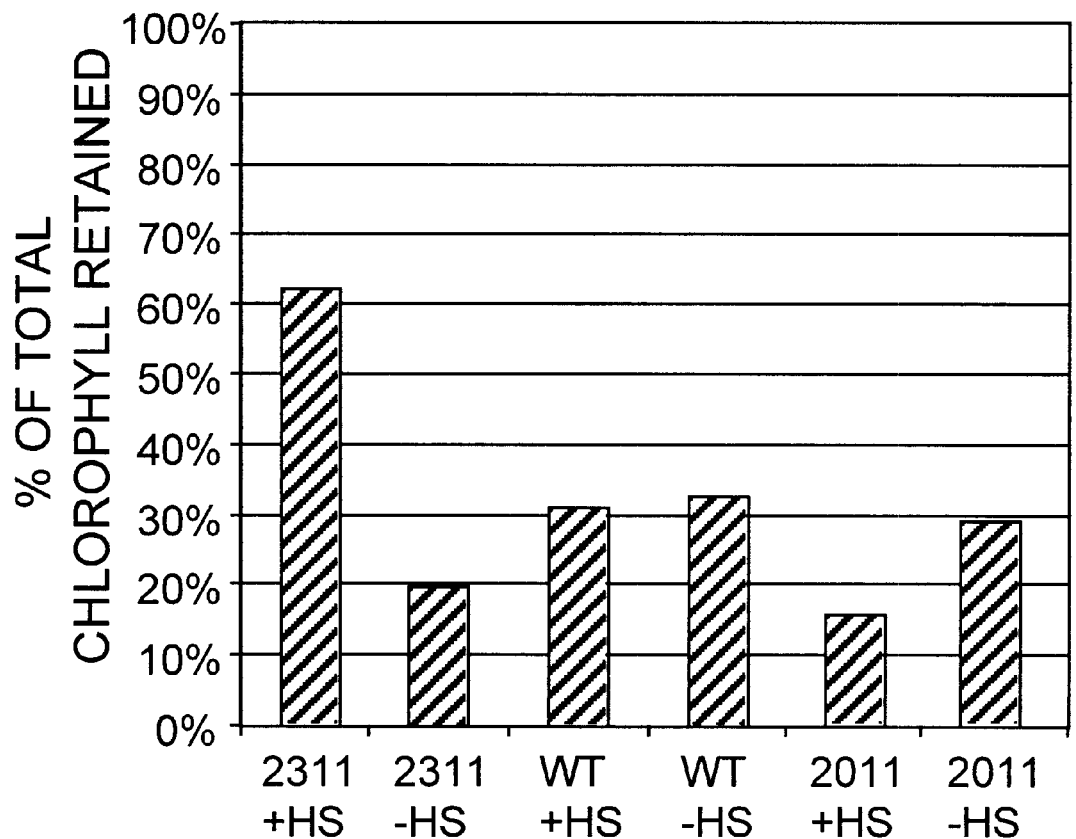

FIG. 10 is a graphical representation of total chlorophyll content. Increased levels of chlorophyll in the C-domain over-expressers indicates a resistance to senescence and increased viability of these plants as compared to wild type and transgenic controls. Total chlorophyll content was determined at 9 after transfer of seedlings to reduced $Ca^{2+}$ medium.

Figure 11:
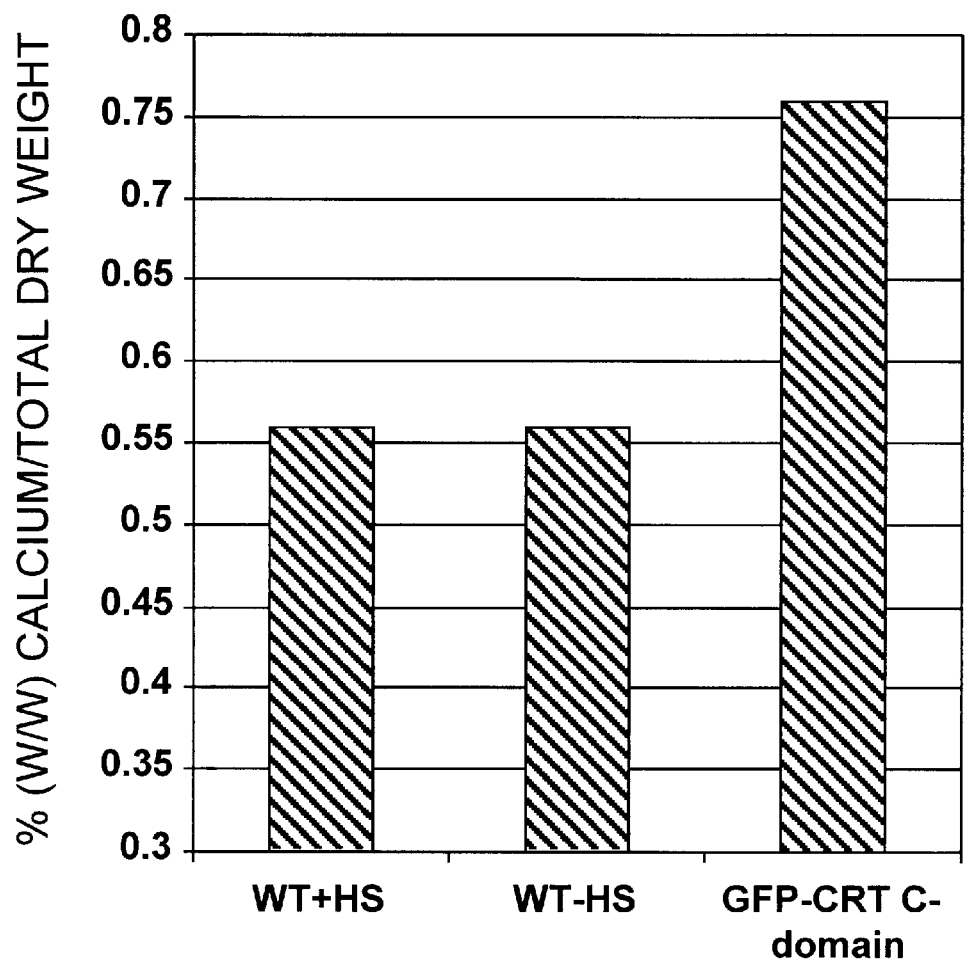

FIG. 11 is a graphical representation demonstrating an increase in total calcium in the CRT C-domain expressers as compared with wild type plants. Seeds from At2311-7 (GFP-CRT C-domain over-expression) and WT were planted on nutrient media and allowed to germinate. Twenty days after germination, seedlings were incubated at 35° C. for 2 hours (heat shock) and allowed to recover at 21° C. overnight. This was repeated on 3 consecutive days. On day 4 the tissue was harvested, washed, and dried. The total calcium content is shown as a percent of the total dry weight of the tissue.

Figure 12:
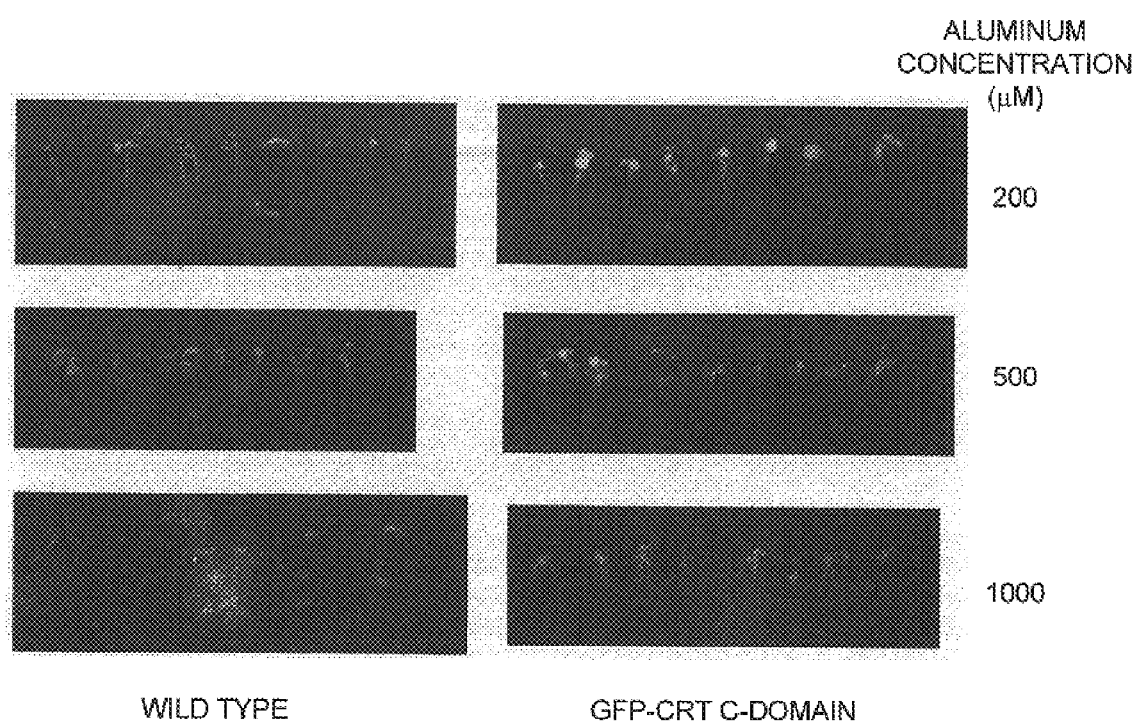

FIG. 12 shows that the expression of the CRT C-domain increases tolerance of Arabidopsis seedlings to high levels of aluminum. Seeds from At2311-4 (GFP-CRT C-domain) (right) and WT (left) were flooded with 200, 500, and 1000 $\mu$M aluminum hydroxide. After 2 hours, the excess liquid was removed and the plants were grown in at 21° C. Pictures were taken 5 days after the treatment.

Figure 13:
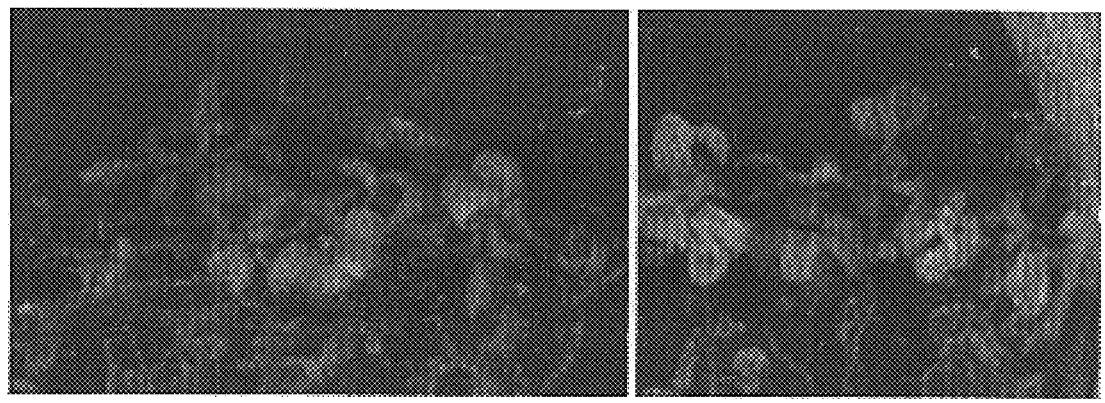

FIG. 13 shows that the expression of the CRT C-domain increases tolerance of Arabidopsis seedlings to 150 mM salt. Seeds from At2311-7 (GFP-CRT C-domain) (left) and At2011 (GFP control) (right) were exposed to 150 mM salt and photographed 30 days after transfer to high salt medium.

Figure 14:
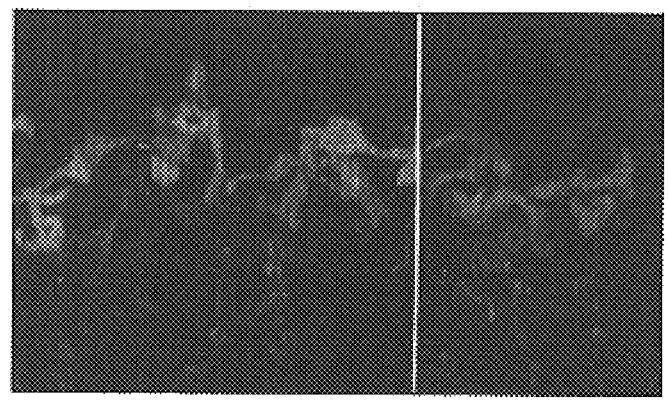

FIG. 14 shows that the expression of the CRT C-domain increases tolerance of Arabidopsis seedlings to 0.2 M salt. Seeds from At2311-7 (GFP-CRT C-domain) (right) and At2011 (GFP control) (left) were exposed to 0.2 M salt and photographed 12 days after transfer to high salt medium.

Figure 15:
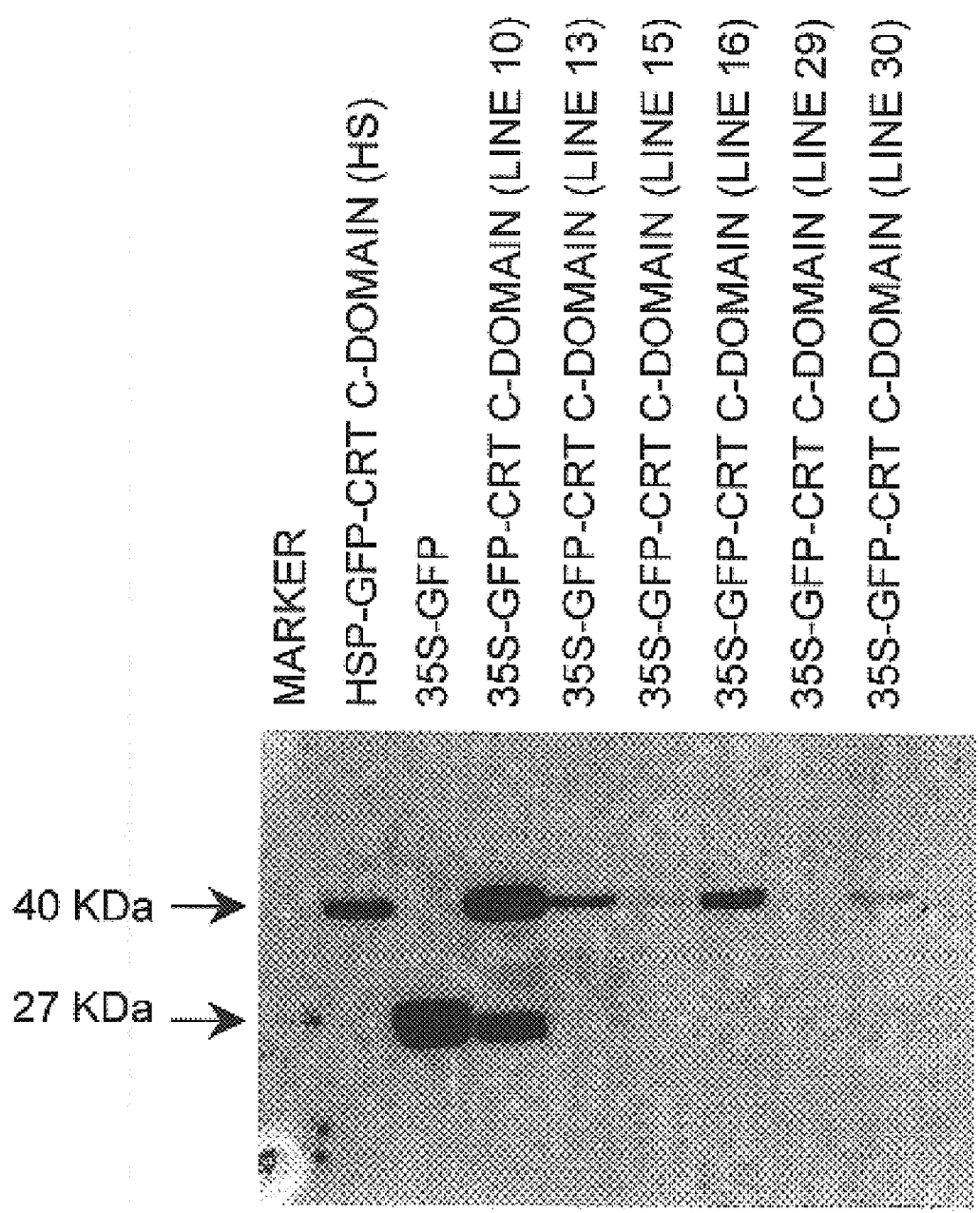

FIG. 15 shows an SDS-PAGE gel of total protein isolated from plants which have constitutive expression of the CRT C-domain in transgenic Arabidopsis. Total protein was extracted from the seedlings, run on SDS-PAGE (2.5 mg tissue/lane), and transferred onto a nitrocellulose membrane. The membrane was probed with polyclonal antibodies against GFP and detected by chemiluminescence. One line (line 10) shows some degradation of the GFP C-domain fusion protein (lane 4) but the others show minimal degradation.

DETAILED DESCRIPTION OF THE INVENTION

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage. Single letter amino acid code is provided for convenience.

Except as otherwise indicated, standard methods may be used for the production of cloned genes, expression cassettes, vectors, proteins and protein fragments, and transformed cells and plants according to the present invention. Such techniques are known to those skilled in the art (see e.g., SAMBROOK et al., EDS., MOLECULAR CLONING: A LABORATORY MANUAL 2d ed. (Cold Spring Harbor, N.Y. 1989); F. M. AUSUBEL et al, EDS., CURRENT PROTOCOLS IN MOLECULAR BIOLOGY (Green Publishing Associates, Inc. and John Wiley & Sons, Inc., New York); J. DRAPER et al., EDS., PLANT GENETIC TRANSFORMATION AND GENE EXPRESSION; A LABORATORY MANUAL, (Blackwell Scientific Publications, 1988); and S. B. GELVIN & R. A. SCHILPEROORT, EDS., INTRODUCTION, EXPRESSION, AND ANALYSIS OF GENE PRODUCTION IN PLANTS.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

The present invention is based, in part, on the discovery that calcium storage in plants may be augmented by the introduction and expression of a transgene expressing a calcium-binding protein. The present inventors have further demonstrated that the increased calcium stores may be in a biologically active form that provides the plant with enhanced tolerance (e.g., improved viability and growth and/or reduced senescence) to conditions of limiting calcium.

As a first aspect, the present invention provides plants expressing a heterologous nucleotide sequence that encodes a calcium-binding protein or peptide (CaBP). The plant may be transiently or stably transformed with the nucleotide sequence encoding the CaBP. Plants that are stably transformed are preferred, with plants providing for germ-line transmission being more preferred. It will be appreciated that not every cell of the plant needs to express the CaBP.

It is further preferred that the transformed plant exhibits normal morphology and is fertile by sexual reproduction. Preferably, transformed plants of the present invention contain a single copy of the transferred nucleic acid, and the transferred nucleic acid has no notable rearrangements therein. Also preferred are plants in which the transferred nucleic acid is present in low copy numbers (i.e., no more than five copies, alternately, no more than three copies, as a further alternative, fewer than three copies of the nucleic acid per transformed cell).

Transformed plants according to the present invention may be from any species, including both dicotyledenous and monocotyledenous plants. Exemplary plants include, but are not limited to corn (*Zea mays*), canola (*Brassica napus, Brassica rapa* ssp.), alfalfa (*Medicago sativa*), rice (*Oryza sativa*), rape (*Brassica napus*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (Cofea spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), apple (*Malus pumila*), blackberry (Rubus), strawberry (Fragaria), walnut (Juglans regia), grape (*Vitis vinifera*), apricot (*Prunus armeniaca*), cherry (Prunus), peach (*Prunus persica*), plum (*Prunus domestica*), pear (*Pyrus communis*), watermelon (*Citrullus vulgaris*). duckweed (Lemna), oats, barley, vegetables, ornamentals, conifers, and turfgrasses (e.g., for ornamental, recreational or forage purposes).

Vegetables include Solanaceous species (e.g., tomatoes; *Lycopersicon esculentum*), lettuce (e.g., *Lactuea sativa*), carrots (*Caucus carota*), cauliflower (*Brassica oleracea*), celery (apium graveolens), eggplant (*Solanum melongena*), asparagus (*Asparagus officinalis*), ochra (*Abelmoschus esculentus*), green beans (*Phaseolus vulgaris*), lima beans (*Phaseolus limensis*), peas (Lathyrus spp.), members of the genus Cucurbita such as Hubbard squash (*C. Hubbard*), Butternut squash (*C. moschata*), zucchini (*C. pepo*), Crookneck squash (*C. crookneck*), *C. argyrosperma, C. argyrosperma* ssp sororia, *C. digitata, C. ecuadorensis, C. foetidissima, C. lundelliana*, and *C. martinezii*, and members of the genus Cucumis such as cucumber (*Cucumis sativus*), cantaloupe (*C. cantalupensis*), and musk melon (*C. melo*).

Ornamentals include azalea (Rhododendron spp.), hydrangea *Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*dianthus caryophyllus*), poinsettia (*Euphorbia pulcherima*), and chrysanthemum.

Conifers which may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Turfgrasses include but are not limited to zoysiagrasses, bentgrasses, fescue grasses, bluegrasses, St. Augustinegrasses, bermudagrasses, bufallograsses, ryegrasses, and orchardgrasses.

Also included are plants that serve as laboratory models, e.g., Arabidopsis.

Preferred plants include vegetables such as legumes and Solanaceous species (e.g., tomatoes), leafy vegetables such as lettuce and cabbage, turfgrasses, and crop plants such as maize, sorghum, cassava, wheat, barley, tobacco, soybeans, cotton and rice.

The present invention also provides tissues (e.g., tubers, roots, vegetative tissue, endosperm, shoot, meristem, and the like), seeds, fruit, and cells, as well as cultured cells and tissues, from the inventive transformed plants.

A. Calcium Binding Proteins

Numerous CaBP are known in the art, and individual members of this super-family are known to possess storage, transport and/or regulatory functions. For example, some CaBP have ATPase activity or are involved in intracellular-signaling cascades. Other CaBP, such as calreticulin (CRT) have both regulatory activities (e.g., chaperonin) and storage functions (in particular, in the C-domain). The C-domain has high capacity/low affinity sites that have been reported to bind about 20–50 moles of calcium per mole of protein. It is known in the art that CaBP are implicated in a multitude of cellular processes and calcium homeostasis is tightly regulated by the plant cell.

It will be further appreciated by those of skill in the art, that the CaBP to be expressed in the plant should be selected so that over-expression thereof does not unduly perturb calcium homeostasis in the cell or plant. Generally, calcium storage proteins are preferred to calcium proteins that have regulatory or signaling activities (e.g., ATPases, calmodulin, and the like). Some CaBP have both storage and signaling/regulatory functions, and the domains that are involved in calcium storage may be expressed independently of the rest of the protein to avoid these regulatory activities or functions. As one particular example, the present inventors have transformed plants with a construct expressing the C-domain of CRT, thereby increasing calcium storage in the plant without the interfering effects of the other domains of the full-length CRT protein.

The CaBP according to the present invention preferably increase (e.g., augment or enhance) the transport or storage of calcium in the plant, or otherwise increase the availability of calcium to the plant. CaBP that increase the storage of calcium in the plant are more preferred. It is also preferred that the CaBP store calcium in a form that is biologically active (i.e., available) to the plant.

In particular embodiments, the CaBP binds more than about 2, 5, 8, 10, or even 15 moles of calcium per mole of protein or peptide. Particular preferred CaBP (e.g., calreticulin or calsequestrin) have been reported to bind as much as 20–50 moles of calcium per mole of protein.

Typically, expression of CaBP according to the present invention will effect an increase in the total calcium content of the plant, although the availability of calcium may be enhanced without an increase in the quantitative amount of calcium in the plant. To illustrate, the introduced CaBP may store calcium in a form that is more biologically active than in wild-type plants. In addition, or as yet a further alternative, the CaBP may enhance transport of calcium to plant tissues that require calcium or enhance the nutritional content of a plant tissue that may be consumed as a source of food or animal feed. The calcium content of the entire plant may be increased, alternatively, the calcium content of particular tissues may be enhanced (e.g., vegetative tissues, roots, growing tissues, seed and/or fruit of the plant, etc.).

In particular preferred embodiments, the expressed CaBP is calreticulin, calsequestrin or a fragment thereof, where the fragment also binds calcium. In more preferred embodiments, the CaBP is the C-domain of CRT or a calcium-binding fragment thereof. The CaBP may alternatively be a fusion protein derived from the calcium-binding regions of one or more CaBP. For example, the CaBP may be a tandem repeat (or other multimer) of the C-domain of CRT, or a fragment of the C-domain fused to a calcium binding domain from another protein.

CRT has been identified in both plant and animals, and the nucleotide and amino acid sequences of plant and animal CRT are known in the art (see, e.g., Genbank Accession numbers M84739, AF177915, AJ000765, AF190454, U66345, U66343, Z71395, and X85382). According to the present invention, CRT proteins, protein fragments, and nucleotide sequences encoding the same may be from any suitable animal or plant source, with plant sources (e.g., maize, tobacco, Arabidopsis, etc.) being preferred.

As described above, in particular preferred embodiments, the expressed CaBP is derived from the C-domain of CRT, a fragment thereof (e.g., an acidic domain, such as a domain that is enriched for Asp or Glu residues), or a multimer of either of the foregoing. Illustrative CaBP have amino acid sequences as given in SEQ ID NO:2 or SEQ ID NO:8, or a calcium-binding fragment thereof. Further exemplary CaBP include proteins and peptides that have at least about 50%, 60%, 65%, 70%, 80%, 90%, 95%, 98% or more homology with SEQ ID NO:2 or SEQ ID NO:8, or fragments thereof. CaBP according to the present invention further encompass truncations, derivatives (e.g., fusion proteins), and multimers of the foregoing sequences.

B. Production of Transgenic Plants with Improved Phenotypic Traits

The transformed plants of the invention may have improved characteristics as a result of expression of the transgene encoding the CaBP. Accordingly, as one further aspect of the present invention is a method of enhancing calcium storage (e.g., calcium content) in a plant by transforming the plant (preferably, stably transforming the plant) with a heterologous nucleotide sequence encoding a CaBP (preferably, CRT, the C-domain of CRT, calsequestrin, or a fragment of any of the foregoing), as described above. According to this embodiment, calcium storage in one or more tissues of the transformed plant is increased as compared with wild-type plants. As set forth above, calcium storage may be increased in all or, alternatively, in less than all of the tissues of the transformed plant. As a further alternative, calcium availability to the plant is improved without increasing calcium content.

The present invention further finds use in methods of enhancing (e.g., increasing, improving, augmenting, and the like) the resistance of a plant to conditions of calcium deficiency. By "conditions of calcium deficiency", as used herein, it is meant that the concentration of available calcium is sub-optimal for plant viability, growth and/or development (e.g., new vegetative growth, flower production, fruit production, fruit ripening, and the like). Conditions of calcium deficiency may result from low concentrations of calcium in the soil and/or water. Alternatively, the availability of calcium to the plant may be reduced as a result of soil pH (e.g., acidic pH), high salt conditions, humidity, or the presence of minerals (e.g., potassium, aluminum, and the like) or chelating agents in the soil that complex with calcium and reduce the bioavailability thereof to the plant. Thus, the inventive plants may further be able to tolerate a greater range of pH and salt conditions than can wild-type plants.

By "enhancing the resistance" of a plant to conditions of calcium deficiency, it is intended that the transformed plant is able to tolerate or withstand conditions of calcium deficiency better than a wild-type plant. For example, the incidence of disease or senescence may be reduced. Likewise, plant viability, flower formation, and/or fruit production may be improved as compared with wild-type plants. By "enhancing the resistance" of a plant to conditions of calcium deficiency, it is not intended to mean that all adverse effects are eliminated, only that the transformed plants are better able to tolerate such conditions than can wild-type plants.

Moreover, the plants of the invention may require less fertilizer supplementation (in particular, calcium supplementation, e.g., applied to the soil, in the water, or by application to the foliage) as compared with wild-type plants. In particular, the transformed plants of the invention may have a reduced need for fertilizer supplementation under conditions of calcium deficiency.

The present invention further finds use in methods of enhancing growth, flower and/or fruit production in a plant, comprising transforming a plant with a heterologous nucleotide sequence encoding a CaBP, as set forth above. In particular embodiments, growth, flower and/or fruit production is enhanced under conditions of calcium deficiency. By "enhancing growth", "enhancing flower production" or "enhancing fruit production", it is meant that these parameters are improved as compared with wild-type plants.

It is known that calcium deficiency is associated with a variety of plant diseases or disorders, including but not limited to, color breakdown (e.g., in Anthurium, sunflowers, beans such as green beans and bush beans), bract necrosis (e.g., in Poinsettia), topple disorder (e.g., in pumpkin, iris), dieback (e.g., in papaya, such as Australia papaya), cavity spot (e.g., in carrots), cork spot (e.g., in brussels sprouts, millet, cowpea, cotton, watermelons, pear), Phytophthora infections (e.g., in soybeans, avocado), adverse effects on carbohydrate composition (e.g., in wheat, pea, coconut), tipburn (e.g., in strawberry, lettuce, cauliflower, cabbage, such as Chinese cabbage), internal rot (e.g., in cabbage, such as Chinese cabbage), erwinia infection (e.g., in carrot), crack and split of fruit (e.g., in apple, tomato, cherry, prune), bitter pit (e.g., in apples, peaches), reduced fruit and seed quality (e.g., in artichoke, cucumber), leaf curl, shoot-tip necrosis (e.g., in potatoes), fruit rot, pod rot (e.g., in Red Spruce, Norway spruce), and blossom end rot (e.g., in tomatoes, sorghum, peppers, eggplant). Other symptoms or diseases associated with calcium deficiency are water soaking of fruits and necrosis of young tissues (e.g., hypocotyl necrosis, death of meristem, and subapical necrosis). Tomatoes, cauliflower, lettuce and other leafy vegetables, and potatoes are particularly susceptible to disease under conditions of calcium deficiency. However, it will be appreciated that the present invention may be employed to reduce the incidence of disease associated with calcium deficiency in any plant.

Accordingly, the present invention further finds use in methods of reducing the incidence of a disease(s) associated with calcium deficiency in a plant by transforming a plant with a heterologous nucleotide sequence encoding a CaBP as described above. By "reducing the incidence" of disease, it is not intended that the transformed plants show no signs of disease associated with calcium deficiency, only that the incidence, rate and/or severity of such disease(s) is decreased as compared with wild-type plants.

As a further aspect, the inventive transformed plants may be better able to withstand (i.e., tolerate) stress, in particular, under conditions of calcium deficiency. The stress may be an environmental stress (hot, cold, draught, hypoosmotic conditions, chemical exposure, high salt conditions, alkaline conditions, acidic conditions, anoxia, and the like), a pathogen-induced stress, disease-induced stress, wounding, or any other source of stress. Thus, the present invention provides methods of enhancing stress resistance in a plant by transforming a plant with a heterologous nucleotide sequence encoding a CaBP as described above. By "enhancing stress resistance", it is not intended that the transformed plants show no adverse effects under stress conditions, only that the incidence, rate and/or severity of such stress-induced effects are decreased as compared with wild-type plants. The effects of stress on a plant may be evaluated or measured by any means known in the art, e.g., by assessing growth, viability, senescence, flower production, fruit production, disease incidence, and the like.

The present inventors have found that plants exhibit signs of senescence under conditions of calcium deficiency. Accordingly, the present invention finds use in methods of reducing senescence in a plant, in particular, under conditions of calcium deficiency, as compared with wild-type plants grown under the same or substantially the same conditions. Alternatively stated, the present invention provides methods of increasing the viability or survival of a plant as compared with wild-type plants, e.g., under conditions of calcium deficiency. Senescence or viability may be measured by any means known in the art. For example, chlorophyll content and leaf color are indicia of senescence. Likewise, viability may be evaluated by chlorophyll content, leaf color, growth, flower production, and the like. The term "reducing senescence" is not intended to indicate that there is no senescence observed in the transformed plants, only that the extent and/or rate of senescence is reduced as compared with wild-type plants. The terms "increasing the viability" or "increasing the survival" of a plant, as used herein, indicates that these parameters are enhanced or improved as compared with wild-type plants.

The present invention further finds use in methods of improving the nutritional content of a plant that serves as a source of animal feed or human food as compared with wild-type plants. In particular embodiments, developmental or tissue-specific expression control sequences (as described below), are used to enhance expression of the heterologous nucleotide sequence encoding the CaBP in a part of the plant that serves as a food or feed source to enhance the calcium content thereof. The plant may be a source of food for humans or animals, including but not limited to, equines, ovines, caprines, bovines, porcines, felines, canines, lagomorphs, rodents (e.g., rats, mice), and avians. In preferred embodiments, the present methods are used to enhance the nutritional content of legumes and fruits (such as soybeans, lettuce, tomatoes), potatoes, cassava, maize, soybeans, turfgrasses used as forage, or grains including wheat, barley, oats, rice and sorghum.

Furthermore, it will be appreciated by those of skill in the art that the foregoing methods of "enhancing calcium storage", "enhancing resistance" to conditions of calcium deficiency or stress, "reducing the incidence disease", etc., may be assessed in connection with a plurality of transformed plants (e.g., a crop, field, greenhouse, or the like). In other words, the effects of enhanced calcium storage, enhanced resistance, reduced incidence of disease, etc., may be achieved collectively in a plurality of plants, although individual plants may not exhibit the improved trait.

C. Expression Cassettes

According to the present invention, the nucleic acid to be transferred is contained within an expression cassette. The plant is transformed with a heterologous nucleotide sequence encoding an expression cassette comprising a sequence encoding a CaBP according to the invention, as described hereinabove. Preferably, the plant is stably transformed. In particular preferred embodiments, the heterologous nucleotide sequence encoding the CaBP comprises a sequence as given in SEQ ID NO:1 or SEQ ID NO:7, or a fragment thereof. Alternatively, the sequence encoding the CaBP is at least about 50%, 60%, 65%, 70%, 80%, 90%, 95%, 98% or more homologous to the sequences given as SEQ ID NO:1 or SEQ ID NO:7 or a fragment thereof.

The heterologous nucleotide sequences according to the present invention also encompass nucleic acid molecules that encode the CaBP of the invention and are substantially homologous to the nucleotide sequences encoding the CaBP molecules disclosed herein, and particularly the isolated nucleotide sequences of SEQ ID NO:1 and SEQ ID NO:7, or continuous nucleotide sequences located therein. This definition is intended to include natural allelic variations in the nucleotide sequences encoding the CaBP. As used herein, regions that are "substantially homologous" are at least about 50%, 60%, 65%, 70%, 80%, 90%, 95%, or even 98% homologous.

The heterologous nucleotide sequences encoding the CaBP may be from any animal or plant species, with plant species being preferred. Isolated nucleotide sequences from other species include those which are at least about 50% homologous (and more preferably are about 60%, 65%, 70%, 80%, 80%, 95%, or even 98% homologous) to the maize CRT C-domain sequences disclosed herein, in particular, sequences given herein as SEQ ID NO:1 or SEQ ID NO:7, or a continuous nucleotide sequence located therein, and which encode a CaBP. Also encompassed are nucleotide sequences encoding the CaBP given as SEQ ID NO:2 or SEQ ID NO:8, but differing therefrom due to the degeneracy of the genetic code.

High stringency hybridization conditions which will permit homologous nucleotide sequences to hybridize to a nucleotide sequence as given herein are well known in the art. For example, hybridization of such sequences to the DNA molecules disclosed herein may be carried out in 25% formamide, 5×SSC, 5×Denhardt's solution, with 100 µg/ml of single-stranded DNA and 5% dextran sulfate at 42° C., with wash conditions of 25% formamide, 5×SSC, 0.1% SDS at 42° C. for 15 minutes, to allow hybridization of sequences of about 60% homology. More stringent conditions are represented by a wash stringency of 0.3 M NaCl, 0.03 M sodium citrate, 0.1% SDS at 60° C. or even 70° C. using a standard hybridization assay (see SAMBROOK et al., EDS., MOLECULAR CLONING: A LABORATORY MANUAL 2d ed. (Cold Spring Harbor, N.Y. 1989). In general, nucleotide sequences that encode CaBP according to the invention and which hybridize to the DNAs encoding the CaBP disclosed herein will be at least about 50% homologous (and more preferably are about 60%, 65%, 70%, 80%, 80%, 95%, or even 98% homologous or more) with the isolated nucleotide sequences disclosed herein.

The heterologous nucleotide sequence may further encode a reporter protein, which may or may not form a fusion protein with the CaBP (e.g., by in-frame ligation of a sequence encoding the reporter protein with the nucleotide sequence encoding the CaBP). Co-transformation with a sequence encoding a reporter protein may advantageously facilitate the detection (e.g., visual detection) of transformed cells in the plant. The heterologous nucleotide sequence may encode any reporter protein suitable for expression and detection in plant cells, including but not limited to green fluorescent protein, β-galactosidase, β-glucoronidase, luciferase, and the like.

In particular embodiments, the heterologous nucleotide sequence may encode a transit peptide (i.e., signal peptide) that localizes the CaBP to a particular subcellular compartment (e.g., plasma membrane, nucleus, lysosome, endoplasmic reticulum, golgi, chloroplast, mitochondrion, vacuole, cytosol, and the like) or directs secretion of the protein. Transit peptides that target protein accumulation in higher plant cells to the chloroplast, mitochondrion, vacuole, nucleus, and the endoplasmic reticulum (for secretion outside of the cell or for retention) are known in the art. Targeting protein expression to the chloroplast (for example, using the transit peptide from the RubP carboxylase small subunit gene) has been shown to result in the accumulation of very high concentrations of recombinant protein in this organelle. Mammalian transit peptides can be used to target recombinant protein expression, for example, to the mitochondrion and endoplasmic reticulum. For example, it has been demonstrated that plant cells recognize mammalian transit peptides that target endoplasmic reticulum (see U.S. Pat. Nos. 5,202,422 and 5,639,947 to Hiatt et al.).

As described hereinbelow, the present inventors have discovered that over-expression of a CRT C-domain transgene fused to an endoplasmic reticulum retention peptide from PR1 (i.e., chitinase) in plants increases the calcium content of the plant and enhances the resistance of the plant to calcium-limiting conditions.

Accordingly, in preferred embodiments, the CaBP will be expressed with an endoplasmic reticulum retention sequence. Exemplary endoplasmic reticulum retention signals include but are not limited to HDEF, HDEL, KDEL, RDEL and KEEL (see, e.g., Kaletta et al., (1998) *FEBS Lett* 4:377–81; Gomord et al., (1997) *Plant J* 11:313–25; Schouten et al., (1996) *Plant Mol Biol* 1996 30:781–93; Denecke et al., (1992) *EMBO J.* 11:2345–55; the disclosures of which are all incorporated herein by reference in their entirety).

In other preferred embodiments, the CaBP may be expressed as a fusion protein with a "carrier" protein or peptide. For example, the carrier protein or peptide may be fused to the CaBP to increase the stability thereof (e.g., decrease the turnover rate) in the cell. Exemplary carrier proteins are glutathione-S-transferase or maltose-binding protein. The carrier protein or peptide may alternatively be a reporter protein, as described. For example, as described above, the fusion protein may encode the CaBP and a reporter protein or peptide (e.g., Green Fluorescent Protein, β-glucuronidase, β-galactosidase, luciferase, and the like) for easy detection of transformed cells and transgene expression. As a further alternative, the fusion protein may encode the CaBP and a carrier protein or peptide that is targeted to a subcellular compartment of interest, i.e., to effect the co-localization of the CaBP. For example, the carrier protein may be a secreted protein, alternatively, a protein that is localized to the plasma membrane, nucleus, lysosome, endoplasmic reticulum, golgi, chloroplast, mitochondrion, vacuole or cytosol. In preferred embodiments, the carrier protein or peptide is targeted to and retained in the endoplasmic reticulum.

Any suitable carrier protein may be expressed as a fusion with the CaBP of the invention. It is preferred, however, that the carrier protein be selected so that over-expression thereof does not have undue adverse effects on the plant.

According to the present invention, the heterologous nucleic acid to be transferred is contained within an expression cassette. The expression cassette comprises a transcriptional initiation region operably associated with the nucleic acid encoding the CaBP. The transcriptional initiation region, (e.g., a promoter) may be native or homologous or foreign or heterologous to the host, or could be the natural sequence or a synthetic sequence. By foreign, it is intended that the transcriptional initiation region is not found in the wild-type host into which the transcriptional initiation region is introduced.

Any suitable promoter known in the art can be employed according to the present invention (including bacterial, yeast, fungal, insect, mammalian, and plant promoters), with plant promoters being preferred. Exemplary promoters include, but are not limited to, the Cauliflower Mosaic Virus 35S promoter, heat shock promoters, the opine synthetase promoters (e.g., nos, mas, ocs, etc.), the ubiquitin promoter, the actin promoter, the ribulose bisphosphate (RubP) carboxylase small subunit promoter, and the alcohol dehydrogenase promoter. Other promoters from viruses that infect plants are also suitable, including but not limited to, promoters isolated from RNA viruses such as Dasheen mosaic virus, Chlorella virus (e.g., the Chlorella virus adenine methyltransferase promoter; Mitra et al., (1994) *Plant Molecular Biology* 26:85), tomato spotted wilt virus, tobacco rattle virus, tobacco necrosis virus, tobacco ring spot virus, tomato ring spot virus, cucumber mosaic virus, peanut stump virus, alfalfa mosaic virus, maize streak virus, figwort mosaic virus, and the like. Promoters from DNA viruses including but not limited to caulimoviruses (e.g., CaMV, FMV), geminiviruses (e.g., MSV and WDV) are also suitable.

Further, expression control elements (e.g., promoters) can be chosen to give a desired level of regulation. For example, in some instances, it may be advantageous to use a promoter that confers constitutive expression (e.g, the CaMV 35S and 19S promoters, the ubiquitin promoter, the RubP carboxylase gene family promoters, and the actin gene family promoters). Alternatively, in other situations, it may be advantageous to use promoters that are activated in response to specific environmental stimuli (e.g., heat shock gene promoters, drought-inducible gene promoters, pathogen-inducible gene promoters, wound-inducible gene promoters, and light/dark-inducible gene promoters) or plant growth regulators (e.g., promoters from genes induced by abscissic acid, auxins, cytokinins, and gibberellic acid).

Developmentally-regulated promoters may also be used, for example, to enhance calcium stores in new growth or ripening fruit. As a further alternative, promoters can be chosen that give tissue-specific expression (e.g., root, shoot, fruit, leaf and/or floral-specific promoters). By "tissue-specific", it is meant that the promoter drives expression of the transgene in less than all tissues of the plant, but not necessarily only in a single tissue.

In other preferred embodiments, a tissue-specific promoter is chosen that will provide for expression of the heterologous sequence encoding the CaBP in a tissue that will be used as a source of food or animal feed. For example, an endosperm-specific promoter may be used in corn plants to increase calcium stores in the corn kernel. In other plants, a promoter that enhances expression in vegetative tissues, flowers, specific organs within the flower, fruit, seeds, or roots is employed.

Organ-specific promoters are also well known. For example, the E8 promoter is only transcriptionally activated during tomato fruit ripening, and can be used to target gene expression in ripening tomato fruit (Deikman and Fischer, *EMBO J* (1988) 7:3315). The activity of the E8 promoter is not limited to tomato fruit, but is thought to be compatible with any system wherein ethylene activates biological processes. Other organ-specific promoters appropriate for a desired target organ can be isolated using known procedures (e.g., subtraction hybridization procedures).

In particular embodiments, the transcriptional cassette includes in the 5'–3' direction of transcription, a transcriptional and translational initiation region, a nucleotide sequence encoding the CaBP, and a transcriptional and translational termination region functional in plants. Any suitable termination sequence known in the art may be used in accordance with the present invention. The termination region may be native with the transcriptional initiation region, may be native with the nucleotide sequence of interest, or may be derived from another source. Convenient termination regions are available from the Ti-plasmid of *A. tumefaciens*, such as the octopine synthetase and nopaline synthetase termination regions. See also, Guerineau et al., *Mol. Gen. Genet.* 262, 141 (1991); Proudfoot, *Cell* 64, 671 (1991); Sanfacon et al., *Genes Dev.* 5,141 (1991); Mogen et al., *Plant Cell* 2, 1261 (1990); Munroe et al., *Gene* 91, 151 (1990); Ballas et al., *Nucleic Acids Res.* 17, 7891 (1989); and Joshi et al., *Nucleic Acids Res.* 15, 9627 (1987). Additional exemplary termination sequences are the pea RubP carboxylase small subunit termination sequence and the Cauliflower Mosaic Virus 35S termination sequence. Other suitable termination sequences will be apparent to those skilled in the art.

Alternatively, the gene(s) of interest can be provided on any other suitable expression cassette known in the art.

The expression cassettes may additionally contain 5' leader sequences. Such leader sequences can act to enhance translation. Translation leaders are known in the art and include: picornavirus leaders, e.g., EMCV leader (Encephalomyocarditis 5' noncoding region; Elroy-Stein et al., *Proc. Natl. Acad. Sci USA,* 86, 6126 (1989)).; potyvirus leaders, e.g., TEV leader (Tobacco Etch Virus; Allison et al., *Virology,* 154, 9 (1986)); human immunoglobulin heavy-chain binding protein (BiP; Macajak and Sarnow, *Nature* 353, 90 (1991)); untranslated leader from the coat protein mRNA of alfalfa mosaic virus (AMV RNA 4; Jobling and Gehrke, *Nature* 325, 622 (1987)); tobacco mosaic virus leader (TMV; Gallie, MOLECULAR BIOLOGY OF RNA, 237–56 (1989)); and maize chlorotic mottle virus leader (MCMV; Lommel et al., *Virology* 81, 382 (1991)). See also, Della-Cioppa et al., *Plant Physiology* 84, 965 (1987). Other methods known to enhance translation can also be utilized, e.g., introns and the like.

Generally, the expression cassette will comprise a selectable marker gene for the selection of transformed cells. Selectable marker genes are utilized for the selection of transformed cells or tissues. Selectable marker genes include genes encoding antibiotic resistance, such as those encoding neomycin phosphotransferase II (NEO) and hygromycin phosphotransferase (HPT), as well as genes conferring resistance to herbicidal compounds. Herbicide resistance genes generally code for a modified target protein insensitive to the herbicide or for an enzyme that degrades or detoxifies the herbicide in the plant before it can act. See, DeBlock et al., *EMBO J.* 6, 2513 (1987); DeBlock et al., *Plant Physiol.* 91, 691 (1989); Fromm et al., *BioTechnology* 8, 833 (1990); Gordon-Kamm et al., *Plant Cell* 2, 603 (1990). For example, resistance to glyphosphate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

For purposes of the present invention, selectable marker genes include, but are not limited to, genes encoding: neomycin phosphotransferase II (Fraley et al., *CRC Critical Reviews in Plant Science* 4, 1 (1986)); cyanamide hydratase (Maier-Greiner et al., *Proc. Natl. Acad. Sci. USA* 88, 4250 (1991)); aspartate kinase; dihydrodipicolinate synthase (Perl et al., *BioTechnology* 11, 715 (1993)); bar gene (Toki et al., *Plant Physiol.* 100, 1503 (1992); Meagher et al., *Crop Sci.* 36, 1367 (1996)); tryptophane decarboxylase (Goddijn et al., *Plant Mol. Biol.* 22, 907 (1993)); neomycin phosphotransferase (NEO; Southern et al., *J. Mol. Appl. Gen.* 1, 327 (1982)); hygromycin phosphotransferase (HP Tor HYG; Shimizu et al., *Mol. Cell. Biol.* 6, 1074 (1986)); dihydrofolate reductase (DHFR; Kwok et al., *Proc. Natl. Acad. Sci. USA* 4552 (1986)); phosphinothricin acetyltransferase (DeBlock et al., *EMBO J.* 6, 2513 (1987)); 2,2-dichloropropionic acid dehalogenase (Buchanan-Wollatron et al., *J. Cell. Biochem.* 13D, 330 (1989)); acetohydroxyacid synthase (U.S. Pat. No. 4,761,373 to Anderson et al.; Haughn et al., *Mol. Gen. Genet.* 221, 266 (1988)); 5-enolpyruvyl-shikimate-phosphate synthase (aroA; Comai et al., *Nature* 317, 741 (1985)); haloaryinitrilase (WO 87/04181 to Stalker et al.); acetyl-coenzyme A carboxylase (Parker et al., *Plant Physiol.* 92, 1220 (1990)); dihydropteroate synthase (sull; Guerineau et al., *Plant Mol. Biol.* 15, 127 (1990)); and 32 kDa photosystem II polypeptide (psbA; Hirschberg et al., *Science* 222, 1346 (1983)).

Also included are genes encoding resistance to: chloramphenicol (Herrera-Estrella et al., *EMBO J.* 2, 987 (1983)); methotrexate (Herrera-Estrella et al., *Nature* 303, 209 (1983); Meijer et al., *Plant Mol. Biol.* 16, 807 (1991)); hygromycin (Waldron et al., *Plant Mol. Biol.* 5, 103 (1985); Zhijian et al., *Plant Science* 108, 219 (1995); Meijer et al., *Plant Mol. Bio.* 16, 807 (1991)); streptomycin (Jones et al., *Mol. Gen. Genet.* 210, 86 (1987)); spectinomycin (Bretagne-Sagnard et al., *Transgenic Res.* 5, 131 (1996)); bleomycin (Hille et al., *Plant Mol. Biol.* 7, 171 (1986)); sulfonamide (Guerineau et al., *Plant Mol. Bio.* 15, 127 (1990); bromoxynil (Stalker et al., *Science* 242, 419 (1988)); 2,4-D (Streber et al., *Bio/Technology* 7, 811 (1989)); phosphinothricin (DeBlock et al., *EMBO J.* 6, 2513 (1987)); spectinomycin (Bretagne-Sagnard and Chupeau, *Transgenic Research* 5, 131 (1996)).

The bar gene confers herbicide resistance to glufosinate-type herbicides, such as phosphinothricin (PPT) or bialaphos, and the like. As noted above, other selectable markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hm1 gene for resistance to the Hc-toxin, and other selective agents used routinely and known to one of ordinary skill in the art. See generally, Yarranton, *Curr. Opin. Biotech.* 3, 506 (1992); Chistopherson et al., *Proc. Natl. Acad. Sci. USA* 89, 6314 (1992); Yao et al., *Cell* 71, 63 (1992); Reznikoff, *Mol. Microbiol.* 6, 2419 (1992); BARKLEY ET AL., THE OPERON 177–220 (1980); Hu et al., *Cell* 48, 555 (1987); Brown et al., *Cell* 49, 603 (1987); Figge et al., *Cell* 52, 713 (1988); Deuschle et al., *Proc. Natl. Acad. Sci. USA* 86, 5400 (1989); Fuerst et al., *Proc. Natl. Acad. Sci. USA* 86, 2549 (1989); Deuschle et al., *Science* 248, 480 (1990); Labow et al., *Mol. Cell. Biol.* 10, 3343 (1990); Zambretti et al., *Proc. Natl. Acad. Sci. USA* 89, 3952 (1992); Baim et al., *Proc. Nati. Acad. Sci. USA* 88, 5072 (1991); Wyborski et al., *Nuc. Acids Res.* 19, 4647 (1991); Hillenand-Wissman, *Topics in Mol. And Struc. Biol.* 10, 143 (1989); Degenkolb et al., *Antimicrob. Agents Chemother* 35, 1591 (1991); Kleinschnidt et al., *Biochemistry* 27, 1094 (1988); Gatz et al., *Plant J.* 2, 397 (1992); Gossen et al., *Proc. Natl. Acad. Sci. USA* 89, 5547 (1992); Oliva et al., *Antimicrob. Agents Chemother.* 36, 913 (1992); HLAVKA ET AL., HANDBOOK OF EXPERIMENTAL PHARMACOLOGY 78 (1985); and Gill et al., *Nature* 334, 721 (1988). Such disclosures are herein incorporated by reference.

The above list of selectable marker genes are not meant to be limiting. Any selectable marker gene can be used in the present invention.

Where appropriate, the selectable marker genes and other gene(s) and nucleic acids of interest to be transferred can be synthesized for optimal expression in the plant of interest. That is, the coding sequence of the genes can be modified to enhance expression in the plant being transformed. The synthetic nucleic acid is designed to be expressed in the transformed tissues and plants at a higher level. The use of optimized selectable marker genes may result in higher transformation efficiency.

Methods for synthetic optimization of genes are available in the art. The nucleotide sequence can be optimized for expression in the plant being transformed. The plant preferred codons may be determined from the codons of highest frequency in the proteins expressed in the plant. Where mammalian, yeast or bacterial genes are used in the invention, they can be synthesized using plant-preferred codons for improved expression. Methods are available in the art for synthesizing plant preferred genes. See, e.g., U.S. Pat. Nos. 5,380,831; 5,436,391; and Murray et al., *Nucleic Acids. Res.* 17:477 (1989); herein incorporated by reference. In addition, genes from mammals, yeast, bacteria and dicots may be optimized for expression in monocots for use in the methods of the invention. See, e.g., EP 0 359 472, EP 0 385 962, WO 91/16432; Perlak et al., *Proc. Natl. Acad. Sci. USA* 88, 3324 (1991), and Murray et al., *Nuc. Acids Res.* 17: 477 (1989), and the like, herein incorporated by reference. It is further recognized that all or any part of the gene sequence may be optimized or synthetic. In other words, fully optimized or partially optimized sequences may also be used.

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The present invention further provides vectors comprising the heterologous sequences encoding the CaBP described herein. Vectors are used herein either to amplify nucleotide sequences encoding proteins or peptides as given herein and/or to express nucleotide sequences which encode proteins or peptides as given herein.

An expression vector is a construct in which a nucleotide sequence encoding a protein or peptide as given herein is operably linked to suitable expression control sequences capable of effecting the expression of the nucleotide sequence in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation.

Typical vectors include, but are not limited to, plasmids, viruses, phage, and integratable DNA fragments (i.e., fragments integratable into the host genome by recombination), bacterial artificial chromosomes, yeast artificial chromosomes, naked DNA vectors, RNA vectors, and hybrid DNA/RNA vectors.

A further aspect of the invention is a host cell containing the vectors of the present invention. Suitable host cells include prokaryote, yeast, plant, and animal cells (e.g., mammalian cells, avian cells, insect cells, and the like). Cells derived from multicellular organisms are a particularly suitable host for recombinant protein or peptide synthesis, and plant, mammalian and insect cells are particularly preferred. Propagation of such cells in cell culture has become a routine procedure (KRUSE & PATTERSON, TISSUE CULTURE, EDS., Academic Press, (1973)).

D. Transformation Methods

Plants can be transformed according to the present invention using any suitable method known in the art. Preferably, the method employed results in stable transfection of the plant. Intact plants, plant tissue, isolated cells, protoplasts, callus tissue, and the like may be used for transformation depending on the plant species and the method employed.

Exemplary transformation methods include biological methods using viruses and Agrobacterium, physicochemical methods such as electroporation, polyethylene glycol, biolistic bombardment, microinjection, and the like. Transformation by biolistic bombardment is preferred.

In one form of direct transformation, the vector is microinjected directly into plant cells by use of micropipettes to mechanically transfer the recombinant DNA (Crossway, *Mol. Gen. Genetics* (1985) 202:179–185).

In another protocol, the genetic material is transferred into the plant cell using polyethylene glycol (Krens, et al. *Nature* (1982) 296:72–74).

In still another method, protoplasts are fused with minicells, cells, lysosomes, or other fusible lipid-surfaced bodies that contain the nucleotide sequence to be transferred to the plant (Fraley, et al., *Proc. Natl. Acad. Sci. USA* (1982) 79:1859–1863).

DNA may also be introduced into the plant cells by electroporation (Fromm et al., *Proc. Natl. Acad. Sci. USA* (1985) 82:5824). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide and regenerate. One advantage of electroporation is that large pieces of DNA, including artificial chromosomes, can be transformed by this method.

Biolistic transformation typically comprises the steps of: (a) providing a plant tissue as a target; (b) propelling a microprojectile carrying the heterologous nucleotide sequence at the plant tissue at a velocity sufficient to pierce the walls of the cells within the tissue and to deposit the nucleotide sequence within a cell of the tissue to thereby provide a transformed tissue. In particular preferred embodiments of the invention, the method further includes the step of culturing the transformed tissue with a selection agent, as described above. In a more preferred embodiment, the selection step is followed by the step of regenerating transformed plants from the transformed tissue. As noted below, the technique could be carried out with the nucleotide sequence as a precipitate (wet or freeze-dried) alone, in place of the aqueous solution containing the nucleotide sequence.

Any biolistic cell transformation apparatus can be used in practicing the present invention. Exemplary apparatus are disclosed by Sandford et al. (*Particulate Science and Technology* 5, 27 (1988)), Klein et al. (*Nature* 327, 70 (1987)), and in EP 0 270 356. Such apparatus have been used to transform maize cells (Klein et al., *Proc. Natl. Acad. Sci. USA* 85, 4305 (1988)), soybean callus (Christou et al., *Plant Physiol.* 87, 671 (1988)), McCabe et al., *BioTechnology* 6, 923 (1988), yeast mitochondria (Johnston et al., *Science* 240, 1538 (1988)), and Chlamydomonas chloroplasts (Boynton et al., *Science* 240, 1534 (1988)).

Alternately, an apparatus configured as described by Klein et al. (*Nature* 70, 327 (1987)) may be utilized. This apparatus comprises a bombardment chamber, which is divided into two separate compartments by an adjustable-height stopping plate. An acceleration tube is mounted on top of the bombardment chamber. A macroprojectile is propelled down the acceleration tube at the stopping plate by a gunpowder charge. The stopping plate has a bore hole formed therein, which is smaller in diameter than the microprojectile. The macroprojectile carries the microprojectile(s), and the macroprojectile is aimed and fired at the bore hole. When the macroprojectile is stopped by the stopping plate, the microprojectile(s) is propelled through the bore hole. The target tissue is positioned in the bombardment chamber so that a microprojectile(s) propelled through the bore hole penetrates the cell walls of the cells in the target tissue and deposit the nucleotide sequence of interest carried thereon in the cells of the target tissue. The bombardment chamber is partially evacuated prior to use to prevent atmospheric drag from unduly slowing the microprojectiles. The chamber is only partially evacuated so that the target tissue is not desiccated during bombardment. A vacuum of between about 400 to about 800 millimeters of mercury is suitable.

In alternate embodiments, biolistic transformation is achieved without use of microprojectiles. For example, an aqueous solution containing the nucleotide sequence of interest as a precipitate could be carried by the macroprojectile (e.g., by placing the aqueous solution directly on the plate-contact end of the macroprojectile without a microprojectile, where it is held by surface tension), and the solution alone propelled at the plant tissue target (e.g., by propelling the macroprojectile down the acceleration tube in the same manner as described above). Other approaches include placing the nucleic acid precipitate itself ("wet" precipitate) or a freeze-dried nucleotide precipitate directly on the plate-contact end of the macroprojectile without a microprojectile. In the absence of a microprojectile, it is believed that the nucleotide sequence must either be propelled at the tissue target at a greater velocity than that needed if carried by a microprojectile, or the nucleotide sequenced caused to travel a shorter distance to the target tissue (or both).

It is currently preferred to carry the nucleotide sequence on a microprojectile. The microprojectile may be formed from any material having sufficient density and cohesiveness to be propelled through the cell wall, given the particle's velocity and the distance the particle must travel. Non-limiting examples of materials for making microprojectiles include metal, glass, silica, ice, polyethylene, polypropylene, polycarbonate, and carbon compounds (e.g., graphite, diamond). Metallic particles are currently preferred. Non-limiting examples of suitable metals include tungsten, gold, and iridium. The particles should be of a size sufficiently small to avoid excessive disruption of the cells they contact in the target tissue, and sufficiently large to provide the inertia required to penetrate to the cell of interest in the target tissue. Particles ranging in diameter from about one-half micrometer to about three micrometers are suitable. Particles need not be spherical, as surface irregularities on the particles may enhance their DNA carrying capacity.

The nucleotide sequence may be immobilized on the particle by precipitation. The precise precipitation parameters employed will vary depending upon factors such as the particle acceleration procedure employed, as is known in the art. The carrier particles may optionally be coated with an encapsulating agents such as polylysine to improve the stability of nucleotide sequences immobilized thereon, as discussed in EP 0 270 356 (column 8).

Alternatively, plants may be transformed using *Agrobacterium tumefaciens* or *Agrobacterium rhizogenes*, preferably *Agrobacterium tumefaciens*. Agrobacterium-mediated gene transfer exploits the natural ability of *A. tumefaciens* and *A. rhizogenes* to transfer DNA into plant chromosomes. Agrobacterium is a plant pathogen that transfers a set of genes encoded in a region called T-DNA of the Ti and Ri plasmids of *A. tumefaciens* and *A. rhizogenes*, respectively, into plant cells. The typical result of transfer of the Ti plasmid is a tumorous growth called a crown gall in which the T-DNA is stably integrated into a host chromosome. Integration of the Ri plasmid into the host chromosomal DNA results in a condition known as "hairy root disease". The ability to cause disease in the host plant can be removed by deletion of the genes in the T-DNA without loss of DNA transfer and integration. The DNA to be transferred is attached to border sequences that define the end points of an integrated T-DNA.

Gene transfer by means of engineered Agrobacterium strains has become routine for many dicotyledonous plants. Some difficulty has been experienced, however, in using Agrobacterium to transform monocotyledonous plants, in particular, cereal plants. However, Agrobacterium mediated transformation has been achieved in several monocot species, including cereal species such as rye (de la Pena et al., *Nature* (1987) 325:274–276), maize (Rhodes et al., *Science* (1988) 240:204–207), and rice (Shimamoto et al., *Nature* (1989) 338:274–276).

While the following discussion will focus on using *A. tumefaciens* to achieve gene transfer in plants, those skilled in the art will appreciate that this discussion also applies to *A. rhizogenes*. Transformation using *A. rhizogenes* has developed analogously to that of *A. tumefaciens* and has been successfully utilized to transform, for example, alfalfa, *Solanum nigrum L.*, and poplar. U.S. Pat. No. 5,777,200 to Ryals et al. As described by U.S. Pat. No. 5,773,693 to Burgess et al., it is preferable to use a disarmed *A. tumefaciens* strain (as described below), however, the wild-type *A. rhizogenes* may be employed. An illustrative strain of *A. Rhizogenes* is strain 15834.

The Agrobacterium strain utilized in the methods of the present invention is modified to contain a gene or genes of interest, or a nucleic acid to be expressed in the transformed cells (e.g., and antisense nucleotide sequence). The heterologous nucleotide sequence to be transferred is incorporated into the T-region and is typically flanked by at least one T-DNA border sequence, preferably two T-DNA border sequences. A variety of Agrobacterium strains are known in the art particularly, and can be used in the methods of the invention. See, e.g., Hooykaas, *Plant Mol. Biol.* 13, 327 (1989); Smith et al., *Crop Science* 35, 301 (1995); Chilton, *Proc. Natl. Acad. Sci. USA* 90, 3119 (1993); Mollony et al., *Monograph Theor. Appl. Genet NY* 19, 148 (1993); Ishida et al., *Nature Biotechnol.* 14, 745 (1996); and Komari et al., *The Plant Journal* 10, 165 (1996), the disclosures of which are incorporated herein by reference.

In addition to the T-region, the Ti (or Ri) plasmid contains a vir region. The vir region is important for efficient transformation, and appears to be species-specific.

Two exemplary classes of recombinant Ti and Ri plasmid vector systems are commonly used in the art. In one class, called "cointegrate," the shuttle vector containing the gene of interest is inserted by genetic recombination into a non-oncogenic Ti plasmid that contains both the cis-acting and trans-acting elements required for plant transformation as, for example, in the PMLJ1 shuttle vector of DeBlock et al., *EMBO J* (1984) 3:1681–1689, and the non-oncogenic Ti plasmid pGV2850 described by Zambryski et al., *EMBO J* (1983) 2:2143–2150. In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan, *Nucleic Acids Research* (1984) 12:8711–8721, and the non-oncogenic Ti plasmid PAL4404 described by Hoekma, et al., *Nature* (1983) 303:179–180.

Binary vector systems have been developed where the manipulated disarmed T-DNA carrying the heterologous nucleotide sequence of interest and the vir functions are present on separate plasmids. In this manner, a modified T-DNA region comprising foreign DNA (the nucleic acid to be transferred) is constructed in a small plasmid that replicates in *E. coli*. This plasmid is transferred conjugatively in a tri-parental mating or via electroporation into *A. tumefaciens* that contains a compatible plasmid with virulence gene sequences. The vir functions are supplied in trans to transfer the T-DNA into the plant genome. Such binary vectors are useful in the practice of the present invention.

In particular embodiments of the invention, super-binary vectors are employed. See, e.g., U.S. Pat. No. 5,591,615 and EP 0 604 662, herein incorporated by reference. Such a super-binary vector has been constructed containing a DNA region originating from the hypervirulence region of the Ti plasmid pTiBo542 (Jin et al., *J. Bacteriol.* 169, 4417 (1987)) contained in a super-virulent *A. tumefaciens* A281 exhibiting extremely high transformation efficiency (Hood et al., *Biotechnol.* 2, 702 (1984); Hood et al., *J. Bacteriol.* 168, 1283 (1986); Komari et al., *J. Bacteriol.* 166, 88 (1986); Jin et al., *J. Bacteriol.* 169, 4417 (1987); Komari, *Plant Science* 60, 223 (1987); ATCC Accession No. 37394.

Exemplary super-binary vectors known to those skilled in the art include pTOK162 (Japanese patent Appl. (Kokai) No. 4-222527, EP 504,869, EP 604,662, and U.S. Pat. No. 5,591,616, herein incorporated by reference) and pTOK233 (Komari, *Plant Cell Reports* 9,303 (1990); Ishida et al., *Nature Biotechnology* 14, 745 (1996); herein incorporated by reference). Other super-binary vectors may be constructed by the methods set forth in the above references. Super-binary vector pTOK162 is capable of replication in both *E. coli* and in *A. tumefaciens*. Additionally, the vector contains the virB, virC and virG genes from the virulence region of pTiBo542. The plasmid also contains an antibiotic resistance gene, a selectable marker gene, and the nucleic acid of interest to be transformed into the plant. The nucleic acid to be inserted into the plant genome is typically located between the two border sequences of the T region. Super-binary vectors of the invention can be constructed having the features described above for pTOK162. The T-region of the super-binary vectors and other vectors for use in the invention are constructed to have restriction sites for the insertion of the genes to be delivered. Alternatively, the DNA to be transformed can be inserted in the T-DNA region of the vector by utilizing in vivo homologous recombination. See, Herrera-Esterella et al., *EMBO J*. 2, 987 (1983); Horch et al., *Science* 223, 496 (1984). Such homologous recombination relies on the fact that the super-binary vector has a region homologous with a region of pBR322 or other similar plasmids. Thus, when the two plasmids are brought together, a desired gene is inserted into the super-binary vector by genetic recombination via the homologous regions.

Plant cells may be transformed with Agrobacteria by any means known in the art, e.g., by co-cultivation with cultured isolated protoplasts, or transformation of intact cells or tissues. The first requires an established culture system that allows for culturing protoplasts and subsequent plant regeneration from cultured protoplasts. Identification of transformed cells or plants is generally accomplished by including a selectable marker in the transforming vector, or by obtaining evidence of successful bacterial infection.

In plants stably transformed by Agrobacterium-mediated transformation, the nucleotide sequence of interest is incorporated into the plant genome, typically flanked by at least one T-DNA border sequence. Preferably, the nucleotide sequence of interest is flanked by two T-DNA border sequences.

Plant cells which have been transformed by any method known in the art can also be regenerated to produce intact plants using known techniques.

Plant regeneration from cultured protoplasts is described in Evans et al., *Handbook of Plant Cell Cultures, Vol. 1:* (MacMilan Publishing Co. New York, 1983); and Vasil I. R. (ed.), *Cell Culture and Somatic Cell Genetics of Plants*, Acad. Press, Orlando, Vol. I, 1984, and Vol. II, 1986). It is known that practically all plants can be regenerated from cultured cells or tissues, including but not limited to, all major species of sugar-cane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently root. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

A large number of plants have been shown capable of regeneration from transformed individual cells to obtain transgenic whole plants.

The regenerated plants selected from those listed are transferred to standard soil conditions and cultivated in a conventional manner. The plants are grown and harvested using conventional procedures.

After the expression cassette is stably incorporated into regenerated transgenic plants, it can be transferred to other plants by sexual crossing. Any of a number of standard breeding techniques can be used, depending upon the species to be crossed.

The particular conditions for transformation, selection and regeneration may be optimized by those of skill in the art. Factors that affect the efficiency of transformation include the species of plant, the tissue infected, composition of the media for tissue culture, selectable marker genes, the length of any of the above-described step, kinds of vectors, and light/dark conditions. Therefore, these and other factors may be varied to determine what is an optimal transformation protocol for any particular plant species. It is recognized that not every species will react in the same manner to the transformation conditions and may require a slightly different modification of the protocols disclosed herein. However, by altering each of the variables, an optimum protocol can be derived for any plant species.

Use of Plants in Salt and Aluminum Contaminated Soil. Plants as used herein may be used for growth in salt or aluminum contaminated soils, where the plants would not otherwise grow, or where the growth of the plants would be adversely affected (e.g., decreased yield) by the salt or aluminum contamination. Plants which are salt and/or aluminum intolerant are particularly suitable for this application of the present invention. By salt or aluminum intolerant is meant that the growth of the parent plant from which the transgenic or recombinant plant is produced is adversely affected in any commercially meaningful manner (for example, decreased yield) by the salt or aluminum contamination of the soil in which the plants of the invention are to be grown. In this method or use of plants of the invention, the plants of the invention are preferably planted together as a crop (i.e., a plurality of plants) in an agricultural field, which agricultural field may be a natural or outdoor field or an indoor field such as in a greenhouse. It will be appreciated that plants need not be rendered perfectly salt or aluminum tolerant by the present invention so long as a useful improvement (e.g., an agriculturally useful improvement) in the salt or aluminum tolerance is imparted thereby.

Aluminum is the most commonly occurring metallic element, comprising eight percent of the earth's crust. The typical range of aluminum in soil is from 1% to 30% by weight (10,000 to 300,000 mg Al kg$^{-1}$), with an average for all soils of 7.1%. In general, aluminum adversely effects plants in its soluble form when soil has an acidic pH, and aluminum contamination is a concern for soils having a pH of 5.5 or less, or a pH of 5 or less. Whether or not a particular aluminum level is considered a contaminant in soil depends upon the aluminum intolerance of the particular plant, as noted above, and will vary from plant to plant. For example, the present invention may be employed with soils having aluminum levels of 5%, 7%, 10%, 15% or 20% or more.

Salt contamination in soil may be measured as soluble salt. In general, whether or not a particular salt level is considered a contaminant in soil depends upon the salt intolerance of the particular plant, as noted above, and will vary from plant to plant. In a soil analysis soluble salt is typically a measure of conductivity of soil solution or the salts which are soluble in water. For example, the present invention may be employed with plants being planted in soils having soluble salt of 0.6 mmhos/cm or more, 0.65 mmhos/cm or more, or 0.7 mmhos/cm or more.

The invention will now be illustrated with reference to certain examples which are included herein for the purposes of illustration only, and which are not intended to be limiting of the invention.

EXAMPLE 1

Materials and Methods

Plasmid Constructions

Figure 5:
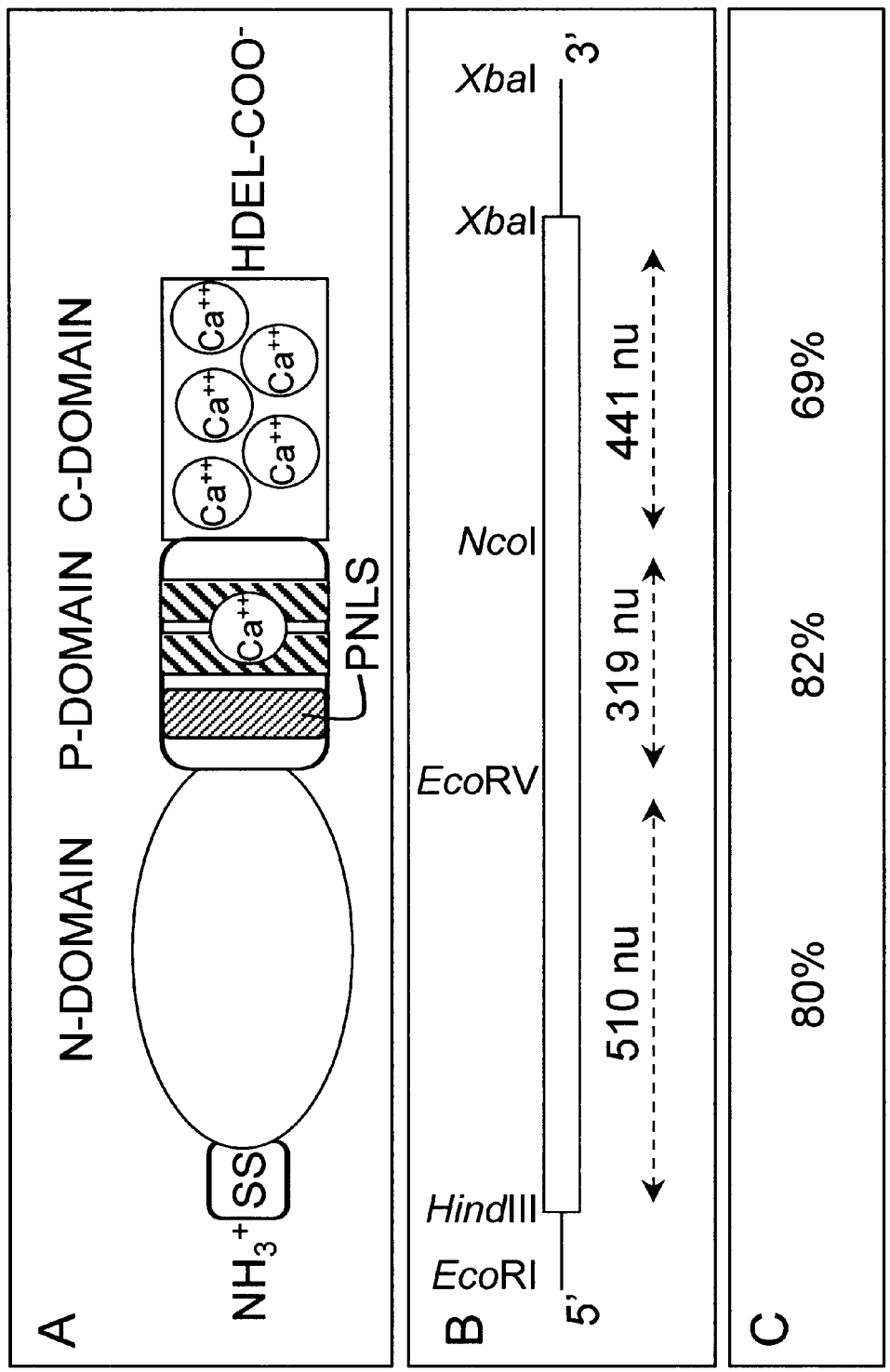
FIG. 5 shows the nucleotide homology of the domains of the maize and Arabidopsis CRT coding sequences.

A full-length CRT cDNA was isolated and sequenced from a maize endosperm library. This sequence (SEQ ID NO:1; GenBank accession AF190454) was used in all CRT-derived constructs (FIG. 1). Alignment of the maize DNA sequence with CRT sequences from other species shows significant homology across species with 73% identity overall between the maize clone and Arabidopsis CRT1, and 69–82% identity in the calcium binding domains (FIG. 5). Alignment of CRT proteins across several species is shown in FIG. 2.

Figure 3:
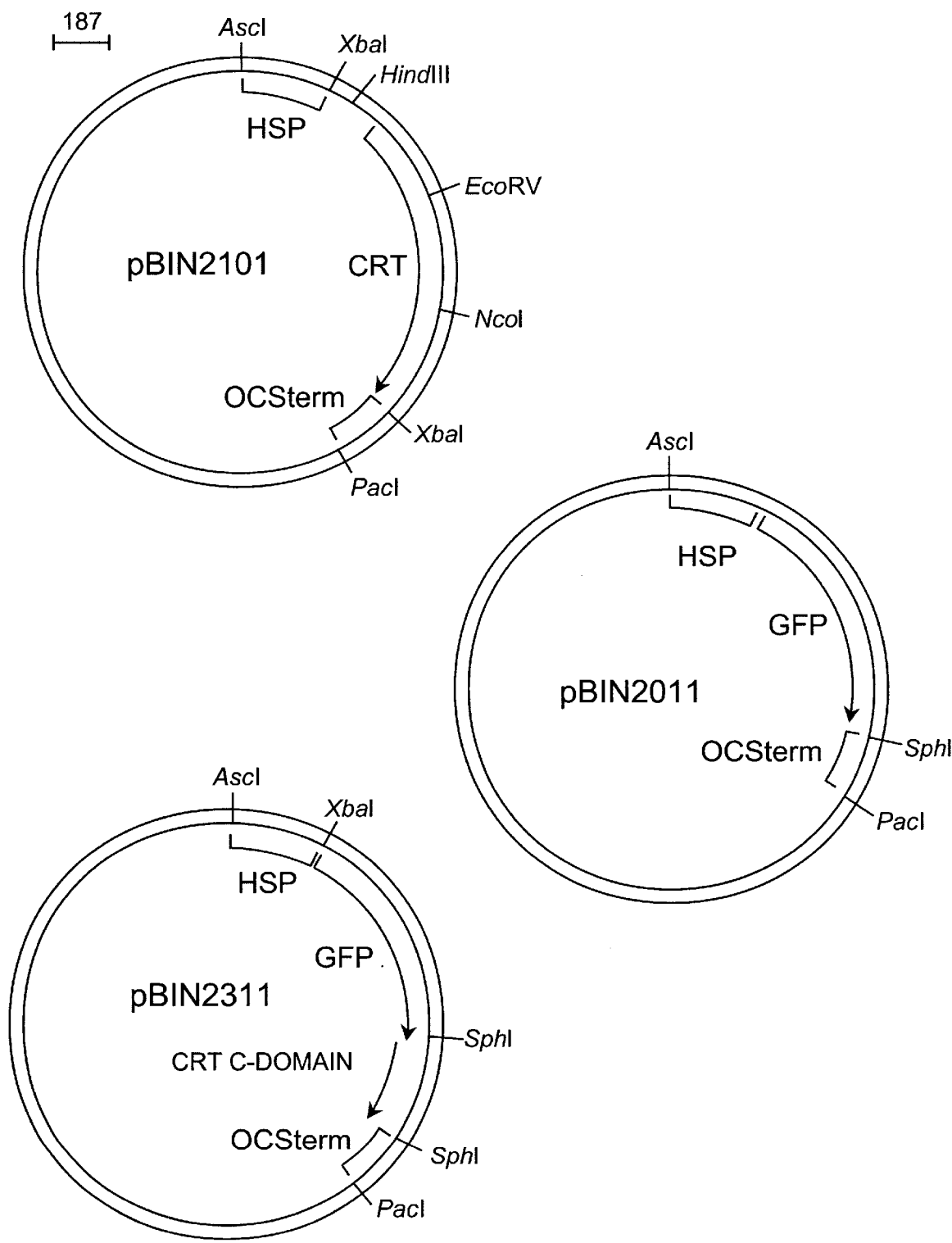
FIG. 3 is a schematic representation of plasmids pBIN2011, pBIN2311 and pBIN2101. All constructs are under control of the Arabidopsis heat shock promoter (AtHSP). pBIN2101 contains a sequence coding for a full-length CRT from maize. pBIN2011 contains the mGFP-5 sequence coding for the green fluorescent protein (GFP). pBIN2311 contains the chimeric mGFP-5-CRT C-domain coding sequence. Both pBIN2011 and pBIN2311 also encode a signal sequence and HDEL ER-retention signal for localization to the ER. A kanamycin resistance cassette in each enables selection of transgenic plants.

The plasmids used for transformation are diagrammed in FIG. 3. The plasmid labeled pBIN2101 is a binary plasmid containing the Arabidopsis heat shock promoter (AtHSP), ocs terminator, and the full-length maize CRT in sense orientation, and was designed as described in Persson et al. (Persson et al., in press). Briefly, the construct consists of a binary plasmid vector containing an Arabidopsis heat shock promoter (AtHSP), followed by a maize endosperm CRT gene in the sense orientation. The AtHSP was inserted into pUCAP (van Engelen et al., (1995) *Transgenic Res.* 4:288) to generate a plasmid containing the AtHSP, a multiple cloning site, and the ocs terminator. The resulting plasmid, labeled pWY2000, was digested with XbaI. A 1365 bp fragment containing the CRT coding sequence and 40 bp of DNA upstream of the start codon was isolated using XbaI, purified and ligated into the pWY2000, creating a sense calreticulin construction, pWY2101, under the control of the AtHSP promoter. The DNA fragments consisting of the AtHSP-CRT-ocs sequence was ligated into the AscI and PacI sites of the binary plasmid vector pBINPLUS (van Engelen et al., (1995) *Transgenic Res.* 4:288) which contains a plant kanamycin resistance cassette. The resulting plasmid was labeled pBIN2101.

To create a CRT C-domain-green fluorescent protein (GFP) fusion, specific PCR primers (5'-GCTCTAGAATGAAGACTAATCTTTTTCT-3'(SEQ ID NO:3) and 5'-GCATGCTGTTTGTATAGTTCATCC-3' (SEQ ID NO:4)) were designed to amplify the ER signal sequence and coding sequence of the GFP gene from pBIN m-gfp5 (Haseloff, J. et al., (1997) *Proc. Nati. Acad. Sci. USA* 94: 2122; described in UK 9504446.7) with the addition of an XbaI site 5' and a SphI site before the HDEL coding sequence. This fragment was ligated into the plasmid pWY2000, containing the Arabidopsis heat shock promoter (AtHSP), multicloning site, and ocs terminator (Persson et al, in press.), digested with XbaI and SphI and the resulting construct was labeled pPLT2013. Specific PCR primers (5'-ACATGCATGCCCCTATGTTGACAACC-3' (SEQ ID NO:5) and 5'-ACATGCATGCCGATCTAGAGCTCGTC-3' (SEQ ID NO:6)) containing SphI sites were designed to amplify a sequence corresponding to the C-domain of the maize CRT gene. The amplified CRT C-domain fragment including the HDEL sequence and the stop codon (FIG. 4; SEQ ID NO:7 and SEQ ID NO:8) was then ligated into pPLT2013 using the SphI site, and the new plasmid was labeled pPLT2311. This clone was sequenced to ensure that the GFP-CRT C-domain fusion was in frame. An AscI, PacI DNA fragment consisting of the AtHSP-GFP-CRT C-domain-ocs sequence was ligated into the AscI and PacI sites of the binary plasmid vector pBINPLUS (van Engelen et al, (1995) *Transgenic Res.* 4:288), and the resulting plasmid was labeled pBIN2311.

To serve as a control, an HSP-mgfp5 construct was designed. The mgfp5 gene encodes an ER-localized GFP protein (Haseloff, (1997) *Proc. Nat. Acad. Sci. USA* 94:2122). The clone pBIN2011 was constructed as described (Persson et al., in press). Briefly, the 35S promoter was removed from plasmid pWY1011 (Scott et al., (1999) *Biotechniques* 26:1127), containing the 35S promoter driving mGFP5 and the ocs terminator, by digestion with HindIII and BamHI. The promoterwas replaced with the AtHSP that had been similarly removed from plasmid pWY2000. The DNA fragment consisting of the AtHSP-mGFP5-ocs sequence was then ligated into the AscI and PacI sites of the binary plasmid vector pBINPLUS to product pBIN2011.

Plant Transformation and Selection

*A. thaliana* plants were transformed using Agrobacterium. Binary vectors pBIN2311, and pBIN2011 were electroporated into *Agrobacterium tumefaciens* strain GV3101 using a Bio-Rad electroporator according to the manufacture's instructions (Bio-Rad, Hercules, Calif.). Wild type *A. thaliana* var. Columbia plants (generation $T_0$) were then transformed by vacuum infiltration as described (Bechtold & Pelletier, (1998) *Methods Mol. Biol.* 82:259; Bechtold et al., (1993) In planta Agrobacterium-mediated gene transfer by infiltration of adult *Arabidopsis thaliana* plants. C. R. Acad. Sci. 316:1194–1199).

Seeds from these plants, labeled generation $T_1$, were sterilized for 30 min in 30% bleach and plated onto AT growth medium [4.3 g/L MS salts (Gibco BRL, Bethesda, Md.), 1×B5 vitamins, 2% sucrose, 0.05% MES pH 5.8, 1% Phytagar (Gibco BRL, Bethesda, Md.)] containing 200 mg/L timetin and 30 mg/L kanamycin. Seedlings were grown for 2 weeks at 21° C. in constant light. Kanamycin resistant seedlings were then transferred to soil and cultivated at 21° C., 8 h light-16 h dark. Seedlings were placed at 35° C. for 2 h for induction of the HSP promoter and then allowed to recover overnight at 21° C. Leaf samples were taken from all plants, weighed, frozen in liquid $N_2$, and stored at −80° C. for analysis of protein expression. Plants were then transferred to a 16 h light-8 h dark regime, allowed to self fertilize, and the resulting seed collected ($T_2$ generation). Progeny were selected from each $T_1$ line that showed a 3:1 ratio of kanamycin resistance consistent with single locus transgene insertion of the transgene.

Analysis of GFP Expression

The $T_2$ generation of plants transformed with pBIN2011 and pBIN2311 were selected for GFP fluorescence. Seedlings were germinated on AT growth medium containing 1% Phytagar (Gibco BRL, Bethesda, Md.). At 5 days after germination, seedlings were incubated for 2 h at 35° C., then allowed to recover overnight at 21° C. prior to imaging. GFP expression was evaluated as described by Scott et al., (1999). *Biotechniques* 26:1127. Fluorescence images were acquired, and those plants showing the brightest GFP fluorescence were selected and grown to seed.

Analysis of Protein Expression

Plants transformed with pBIN2311 were also analyzed for GFP expression by Western blot analysis (F. M. AUSUBEL et al, (1992) CURRENT PROTOCOLS IN MOLECULAR BIOLOGY, Green Publishing Associates, Inc. and John Wiley & Sons, Inc., New York). Approximately 20–50 mg samples of young leaves were collected from each plant, weighed, and frozen in liquid nitrogen. Leaves were ground in 2× sample buffer (Ausubel et al., supra) using 1 µl of buffer to 1 mg of plant material. Equal amounts of plant tissue were loaded into each lane of a 10% SDS polyacrylamide gel, and proteins were separated by electrophoresis. Separated proteins were either stained with Gelcode Blue (Pierce, Rockford, Ill.) or transferred to a nitrocellulose membrane (Bio-Rad, Bethesda, Md.) using a Bio-Rad Mini Trans-Blot Assembly. Proteins were detected using polyclonal antibodies against recombinant GFP (Clontech, Palo Alto, Calif.) diluted 1:1000 and horseradish peroxidase-conjugated secondary antibodies using a chemiluminescent substrate (Roche Biochemical, Indianapolis, Ind.) according to the manufacturer's instructions.

Assessment of Seedling Viability

Seeds of each line T3 were germinated on normal AT growth media. On day 16, 17, and 18 after germination the seedlings were incubated at 35° C. for 2 hours each day to induce expression of the transgene. On day 19, Parafilm was removed from the plates for 6 hours, and the plates opened in a laminar flow hood for 30 min to increase the transpiration rate and calcium uptake. The seedlings were then transferred to fresh AT growth medium with or without 10 mM ethylene Glycol-bis(α-aminoethyl ether) N,N,N',N'-tetraacetic Acid (EGTA), or AT growth media with 12 mM $CaCl_2$+10 mM EGTA. Images of these plants were taken at 3-day intervals until 12 days after transfer. At day 9 and day 12, seedlings were sacrificed for determination of chlorophyll content. The shoot of each plant was removed, weighed, and place in an Eppendorf tube containing 1 ml of N,N-dimethylformamide. Total chlorophyll was determined according to Moran, (1982) Plant Physiology 69:1376.

Total Calcium Measurement

200–300 seeds of each line were germinated on normal AT growth medium. Transgene expression was induced as above and on day 19, whole seedlings were harvested. These tissues were rinsed with deionized water to remove excess medium. The tissues were then dried at 50° C. overnight and weighed. One gram of dried tissue from each line was analyzed for total calcium using a Perkin-Elmer Plasma 2000 System spectrometer (Perkin Elmer Corp., Norwalk, Conn.) at the Analytical Services Laboratory at North Carolina State University.

EXAMPLE 2

Results

The Calreticulin Clone

CRT is conserved in plants and animals. Our goal was to produce stable transgenic lines that could be induced for CRT expression. Therefore, we identified a closely related plant CRT from maize that was expected to have similar properties to the Arabidopsis CRT.

A schematic of the nucleotide identity between the nucleotide sequences of the maize and Arabidopsis CRTs is shown in FIG. 5. Both sequences encode a signal sequence and HDEL retention signal for ER localization. Alignment of the maize and Arabidopsis DNA sequences of CRT shows significant homology across species with 73% identity overall between the maize clone and Arabidopsis CRT1 (Nelson et al., (1997) *Plant Physiol.* 114:29) and 69–82% identity in the calcium binding domains.

Expression of CRT in Arabidopsis

The maize CRT clone was used to express full-length calreticulin in both sense orientations under control of an Arabidopsis heat shock promoter. Transgenic lines of Arabidopsis, At2101-3 have been selected as pure lines that over-express CRT based on Western blot analysis of CRT protein expression after heat shock (FIG. 6). The resultant seedlings show no obvious phenotype when germinated and grown on normal calcium (2 mM) media. However, when grown on low calcium (10 mM EGTA) media, phenotypic differences become detectable. The most obvious difference is an increase in viability of the At2101 over-expressers with time on the low calcium media. The CRT over-expressers were viable up to 10 days after transfer to low calcium media whereas WT plants were virtually dead by 6 days These data are consistent with the hypothesis that over-expression of CRT does increase $Ca^{2+}$ stores and, thereby, increase viability under $Ca^{2+}$ stress conditions. However, it is difficult from these data to attribute the increased viability to increased calcium storage alone. The response may be an effect of other functions of CRT. To address this question, we engineered plants that express only the C-domain of CRT rather than the entire protein.

Expression of the CRT C-Domain

Figure 7:
FIG. 7 shows photographs of Arabidopsis seedlings expressing the GFP-CRT C-domain fusion protein. Panel A) GFP expression under control of the heat shock promoter is visible in both roots and shoots of wild type (left) and At2311 (GFP-CRT C-domain expresser) (right). Panel B) Construct expression is localized to the endoplasmic reticulum. Seedlings were plated onto nutrient medium and allowed to germinate. Five days after germination, seedlings were incubated at 35° C. for 2 h (heat shock) and allowed to recover at 21° C. overnight. Plants were photographed on day 2 after heat shock. Images were taken on a (A) Leica stereomicroscope (Excitation: 450–490 nm, Emission: >510 nm), (B).
Figure 8:
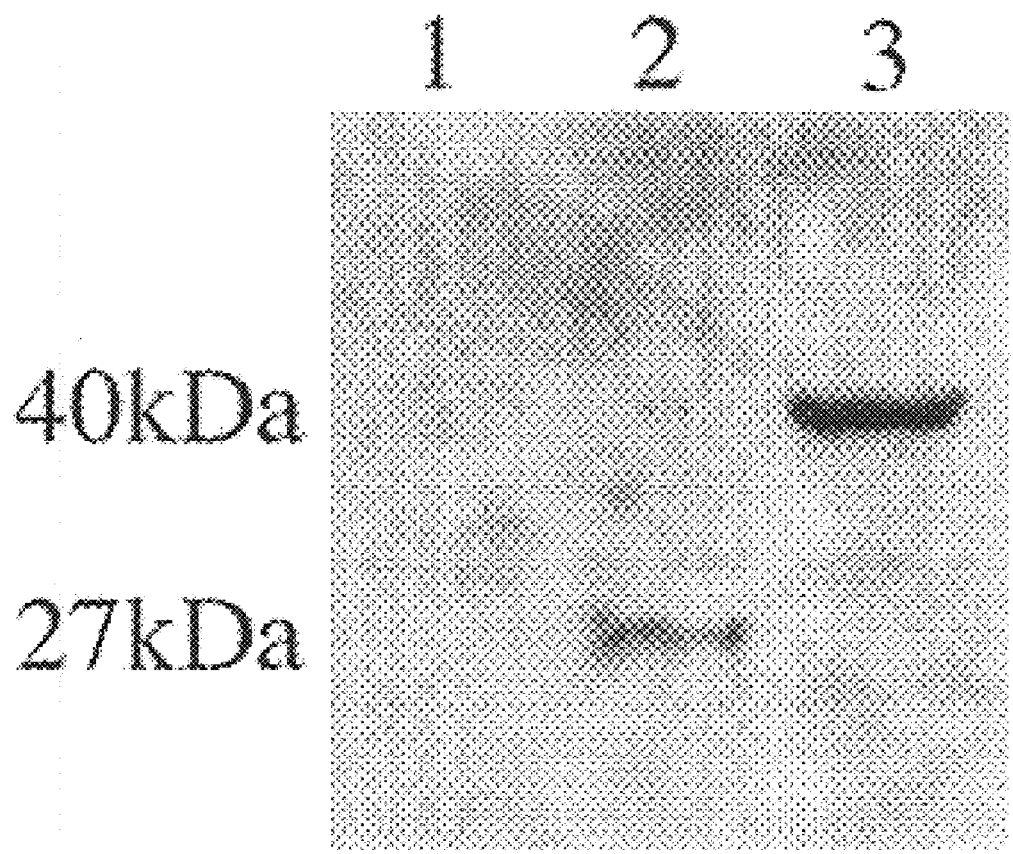
FIG. 8 presents Western blot analysis indicating the appropriate size shift for the GFP-CRT C-domain fusion.

The C-domain of CRT is a low affinity ($K_d$=0.3–2 mM), high capacity $Ca^{2+}$ binding peptide which can bind as much as 20–50 moles of $Ca^{2+}$ per mole of peptide (Michalak et al., (1992) *Biochem. J.* 285:681). The C-domain sequence was cloned as a fusion to the green fluorescent protein (GFP) to be able to track expression within the plant. The fusion protein was targeted to the ER as was a GFP control, both under control of the Arabidopsis heat shock promoter (FIG. 7). Transgenic lines of Arabidopsis, At2311-7 and At2011-1 have been selected as pure lines that over-express the CRT-C-domain-GFP fusion and ER-targeted GFP, respectively, based on GFP expression after heat shock. GFP expression is visible in both shoot and root tissues under control of the heat shock promoter (FIG. 7). Western blot analysis, using antibodies directed against GFP, indicated the appropriate size shift for the GFP-CRT C-domain fusion (FIG. 8).

Seedling Phenotype

The seedlings expressing the GFP-CRT C-domain fusion show no obvious phenotype when germinated and grown on normal calcium (2 mM) medium (FIG. 9; panel A). However, when grown on low calcium (10 mM EGTA), phenotypic differences become detectable. The most obvious difference is the ability of the At2311-7, containing the GFP-CRT C-domain fusion, to resist senescence with time on reduced calcium media. By day 9 after transfer to reduced calcium media, the WT plants were yellowing and stunted whereas plants from line At2311-7 were still green and viable (FIG. 9; panel B). Measurements of total chlorophyll indicated that plants from line At2311-7 maintained as much as 87% of their chlorophyll after 9–12 days on reduced calcium medium whereas wt and transgenic GFP controls retained approximately 50% (FIG. 10). However under continued stress, plants from line At2311-7 also lost chlorophyll, suggesting that the increased stored calcium had been depleted.

To determine if ectopic expression of the CRT C-domain caused an increase in total calcium or whether calcium was simply reallocated to the ER, we measured the total calcium content of the seedlings. Plants from line At2311-7 showed on average a 9% increase in total plant calcium compared to wild plants and transgenic GFP control plants (FIG. 11). These data clearly support our hypothesis that the increased viability of the transgenic plants on reduced calcium media is due to increased stores of ER calcium sequestered during growth on normal medium.

In these experiments, the C-domain of CRT was used as a reagent to alter calcium storage within the ER. The C-domain was specifically isolated in order to avoid potentially confounding interactions resulting from other regions of the protein. Using transgenic plants expressing this ER-localized peptide, we showed that seedlings germinated in calcium-containing medium and then transferred to medium lacking calcium have enhanced survival. This result is apparently because of their ability to store extra calcium, and for that calcium to serve as a reserve when external calcium concentrations are low.

The foregoing studies have demonstrated (1) the ability to increase calcium storage in Arabidopsis expressing an ER-targeted peptide derived from the C-domain of CRT, and (2) an apparent ability of the transgenic plants to access these stores under calcium stress conditions.

EXAMPLE 3

Evaluation of Arabidopsis Expressing the C-Domain of CRT to Stress

Aluminum Stress

T3 seeds of line At2311-4 (GFP-CRT C-domain) and wild type control plants were germinated on growth medium which consists of macronutrients (Table 1), micronutrients (Table 2), 1% Sucrose, and 0.8% Type M Agar (pH adjusted to 4.3) and grown at 21° C. For 2 days, the seedlings were incubated at 35° C. for 2 hours each day to induce the expression of the transgene, then returned to 21° C. to allow recovery. On day 3, plates were flooded with 200 μM, 500 μM or 1 mM aluminum hydroxide for 2 hours. Then the excess solution was removed. The plates were placed back into the growth chamber at 21° C. Images of these plants were taken 5 days after treatment with aluminum.

TABLE 1

| Salt | Final Conc. | Fm Wt | 40 L 50 X |
|---|---|---|---|
| $KNO_3$ | 2 mM | 101 | 8.08 g |
| $KH_2PO_4$ | 0.1 mM | 136 | 0.544 g |
| $MgSO_4$ | 2 mM | 246.5 | 19.72 g |
| $(NH_4)_2SO_4$ | 0.25 mM | 132 | 1.32 g |
| $Ca(NO_3)_2$ | 1 mM | 236 | 9.44 g |
| $CaSO_4$ | 1 mM | 136 | 5.44 g |
| $K_2SO_4$ | 1 mM | 174 | 6.96 g |

TABLE 2

| Salt | Final Conc. | Fm Wt | 50 L 50 X |
|---|---|---|---|
| $MmSO_4$ | 1 μM | 169 | 8.45 mg |
| $H_3BO_3$ | 5 μM | 61.8 | 15.45 mg |
| $CuSO_4$ | 0.05 μM | 249.7 | 0.624 mg |
| $ZnSO_4$ | 0.2 μM | 287.5 | 2.875 mg |
| $NaMoO_4$ | 0.02 μM | 242 | 0.242 mg |
| $CoCl_2$ | 0.1 μM | 147 | 0.735 mg |
| $K_2SO_4$ | 0.001 μM | 238 | 0.119 mg |

Both lines showed stress after the $Al^{3+}$ treatment but At2311-4, containing the GFP-CRT C-domain fusion protein, grew better and larger in size compared to the control WT plants. FIG. 12 shows the plants 5 days after the $Al^{3+}$ treatment, the control WT plants were not able to germinate well as plants from line At2311-4 were still green.

Salt Stress

T3 seeds of line At2311-7 (GFP-CRT C-domain) and control At2011-1 (GFP) were germinated on normal AT growth medium and grown for 8 days at 21° C. At days 9, 10, and 11, the seedlings were incubated at 35° C. for 2 hours each day to induce the expression of the transgene, then returned to 21° C. to allow recovery. On day 12, seedlings were transferred onto high salt medium (normal AT medium+150 mM or 200 mM NaCl). Plants of each line were placed on the same plate. These plates were placed vertically in the growth chamber at 21° C. Images of these plants were taken 12 days to 1 month after transfer.

Both lines showed stress when grown on high salt medium, but At2311-7 containing the GFP-CRT C-domain fusion protein, showed delayed senescence compared to the control line At2011-1 on high salt medium. One month after transfer to 150 mM salt medium, the control plants (At2011-1) were chlorotic whereas plants from line At2311-7 were still green (FIG. 13). The difference in chlorosis was less dramatic on 200 mM NaCl (FIG. 14) suggesting that both the C-domain and the GFP control plants were stressed. Previous studies demonstrated that increased $Ca^{2+}$ inhibits $Na^+$ influx but $K^+/Na^+$ selectivity is maintained in plants (Cramer et al., 1987). Earlier results showed that by expressing the GFP-CRT C-domain fusion protein, total plant calcium levels increased (Wyatt et al., in press). Result presented herein suggest that plants expressing the GFP-CRT C-domain have a higher viability and as measured by a higher chlorophyll level under continued salt stress.

Transformed Arabidopsis expressing the C-domain of CRT, as described in Example 1 above, are crossed with an Arabidopsis line transformed with a gene encoding a reporter protein operably linked to an alcohol dehydrogenase (ADH) promoter. The ADH promoter in plants has been reported to be induced in response to stress stimuli, e.g., anoxia.

Hybrid (C-domain/ADH reporter) plants and ADH transformants are subjected to stress, (e.g., cold, heat, drought, high salinity, anoxia, pathogens, alkaline, acidic conditions, and the like, as well as including growth in agar, liquid medium, and air). The plants are assessed for stress response based on induction of the reporter gene driven by the ADH promoter. The hybrid plants are evaluated for stress resistance (i.e., reduced ADH promoter induction) in the presence of expression of the C-domain of CRT.

The ADH promoter can be differentially activated in roots and shoots, and calcium is known to be involved in transduction of signals from the root that activate ADH promoter activity in shoots. Previous studies showed that growth in medium containing EGTA prevented transduction of a signal caused by anoxia. Expression of the CRT C-domain may increase calcium available for root to shoot signaling.

In other studies, Arabidopsis expressing the C-domain of CRT as described in Example 1 and wild-type controls are subjected to stress (e.g., cold, heat, drought, high salinity, anoxia, pathogens, alkaline, acidic conditions, and the like, as well as growth in agar, liquid medium, and air) and observed for stress response. Response to stress may be assessed by any suitable measure, e.g., chlorophyll content, growth, and the like.

EXAMPLE 4

Constitutive Expression of a GFP-CRT C-Domain Fusion Protein

The 35S promoter region of clone pBIN mGFP5 was isolated out by using the HindIII and BamHI sites. The HindIII and BamHI DNA fragment consisting of the 35S promoter sequence was ligated into the HindIII and BamHI sites of plasmid pPLT2311 (Wyatt et al., in press). The original pPLT2311 contains the HindIII site at the 5' end and a BamHI site at the 3' end of the HSP promoter region. This HSP promoter was removed and replaced with the 35S promoter to promote constitutive expression of the GFP-C-domain fusion protein. The new plasmid was designated pPLT1311. Plasmid pPLT1311 was sequenced to ensure that the GFP-CRT C-domain fusion was in frame. An Ascl, Pacl DNA fragment consisting of the At 35S-GFP-CRT C-domain-ocs sequence was ligated into the Ascl and Pacl sites of the binary plasmid vector pBINPLUS (van Engelen et al, 1995), and the resulting plasmid was labeled pBIN1311. Plants were transformed with pBIN1311 as described in EXAMPLE 1, with the exception of timetin being added to the AT medium.

Constitutive expression of a GFP-C-domain fusion protein in the ER of plants may affect plant growth by altering intracellular calcium homeostasis. Seed from 10 independent transgenic lines containing a 35S GFP-C-domain construct were tested. The level of fusion protein differed in the 10 lines, consistent with position effect variation often reported in transgenic plants. The level of protein in some lines was similar to the level of protein produced following heat shock induction of the same gene controlled by a heat shock promoter (Wyatt et al., in press; FIG. 15) but was lower than that produced by a 35S-GFP control line. Line 10 showed high levels of expression of the GFP C-domain construct, but also showed accumulation of a degradation product similar in size to GFP.

Phenotypic analysis of all 10 lines demonstrated that growth rate and morphology was similar to non-transgenic control plants. No detectable differences in flowering and seed set were noticed in the transgenic plants. These studies demonstrate that constitutive expression of the C-domain GFP fusion is not deleterious to plants under normal growth conditions.

EXAMPLE 5

Transformation of Maize with CRT

Maize plants are transformed with the C-domain construct operably associated with a maize UB1 promoter by biolistic transformation using standard techniques known in the art. Stable transformants are regenerated and assessed for phenotypic effects of the over-expression of the C-domain of CRT.

Transformed maize plants are evaluated for total calcium content, resistance to conditions of calcium deficiency, and stress resistance as described in Examples 1–3 above. Calcium content of the corn kernel is also assessed.

In a further set of studies, a construct comprising the C-domain of CRT operably-associated with an endosperm-specific promoter is used to transform maize plants, and the calcium content of the kernels of transformed plants is assessed.

Using standard techniques, the calcium stores of the corn kernels produced by the transformed maize plants described above are analyzed to determine the chemical form of the calcium. The bioavailability of different chemical forms of calcium in feed and food for animals is known in the art. The biological activity of the calcium stores may further be assessed using standard nutritional studies in animal or human subjects.

Although the foregoing invention has been described in some detail by way of illustration and example for purposes of clarity of understanding, it will be obvious that certain changes and modifications may be practiced within the scope of the appended claims.

That which is claimed is:

1. A plant comprising a heterologous nucleotide sequence that encodes an amino acid sequence comprising the amino acid sequence of SEQ ID NO:8.

2. The plant of claim 1, wherein the heterologous nucleotide sequence is selected from the group consisting of the nucleotide sequence of SEQ ID NO:7 and a nucleotide sequence that hybridizes with the complement of the nucleotide sequence of SEQ ID NO:7 under conditions of high stringency and encodes a calcium binding protein.

3. A plant comprising a heterologous nucleotide sequence that encodes an amino acid sequence comprising the amino acid sequence of SEQ ID NO:2.

4. The plant of claim 3, wherein the heterologous nucleotide sequence is selected from the group consisting of the nucleotide sequence of SEQ ID NO:1 and a nucleotide sequence that hybridizes with the complement of the nucleotide sequence of SEQ ID NO:1 under conditions of high stringency and encodes a calcium binding protein.

5. The plant of claim 1, further comprising a nucleotide sequence that encodes a carrier protein or peptide.

6. The plant of claim 5, wherein the carrier protein or peptide is selected from the group consisting of green fluorescent protein, glutathione-S-transferase, and maltose binding protein.

7. The plant of claim 1, further comprising a nucleotide sequence that encodes a signal sequence that directs the product of the heterologous nucleotide sequence to a subcellular compartment.

8. The plant of claim 1, further comprising a nucleotide sequence that encodes a reporter protein or peptide.

9. The plant of claim 8, wherein the nucleotide sequence encoding a reporter protein or peptide is selected from the group consisting of neo, bar, pat, ALS, HPH, HYG, EPSP and Hm1.

10. The plant of claim 1, wherein the heterologous nucleotide sequence is expressed in the plant to produce a calcium binding protein that binds more than about five moles of calcium per mole of protein.

11. Seed produced by the plant of claim 1, wherein the seed comprises the heterologous nucleotide sequence.

12. Fruit produced by the plant of claim 1, wherein the fruit comprises the heterologous nucleotide sequence.

13. A plant tissue from the plant of claim 1, wherein the plant tissue comprises the heterologous nucleotide sequence.

14. The plant of claim 3, further comprising a nucleotide sequence that encodes a carrier protein or peptide.

15. The plant of claim 14, wherein the carrier protein or peptide is selected from the group consisting of green fluorescent protein, glutathione-S-transferase, and maltose binding protein.

16. The plant of claim 3, further comprising a nucleotide sequence that encodes a signal sequence that directs the product of the heterologous nucleotide sequence to a subcellular compartment.

17. The plant of claim 3, further comprising a nucleotide sequence that encodes a reporter protein or peptide.

18. The plant of claim 17, wherein the nucleotide sequence encoding a reporter protein or peptide is selected from the group consisting of neo, bar, pat, ALS, HPH, HYG, EPSP and Hm1.

19. The plant of claim 3, wherein the heterologous nucleotide sequence is expressed in the plant to produce a calcium binding protein that binds more than about five moles of calcium per mole of protein.

20. Seed produced by the plant of claim 3, wherein the seed comprises the heterologous nucleotide sequence.

21. Fruit produced by the plant of claim 3, wherein the fruit comprises the heterologous nucleotide sequence.

22. A plant tissue from the plant of claim 3, wherein the plant tissue comprises the heterologous nucleotide sequence.

* * * * *